(12) United States Patent
Fujita et al.

(10) Patent No.: US 11,050,931 B2
(45) Date of Patent: Jun. 29, 2021

(54) CONTROL DEVICE AND CONTROL METHOD

(71) Applicant: SONY CORPORATION, Tokyo (JP)

(72) Inventors: Goro Fujita, Kanagawa (JP); Tetsuro Kuwayama, Tokyo (JP); Takeshi Matsui, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/611,516

(22) PCT Filed: Apr. 18, 2018

(86) PCT No.: PCT/JP2018/015959
§ 371 (c)(1),
(2) Date: Nov. 7, 2019

(87) PCT Pub. No.: WO2018/211902
PCT Pub. Date: Nov. 22, 2018

(65) Prior Publication Data
US 2020/0112673 A1    Apr. 9, 2020

(30) Foreign Application Priority Data

May 16, 2017  (JP) .............................. JP2017-097151

(51) Int. Cl.
*A61B 5/06*       (2006.01)
*H04N 5/232*   (2006.01)
(Continued)

(52) U.S. Cl.
CPC ......... *H04N 5/23235* (2013.01); *A61B 1/063* (2013.01); *A61B 5/0261* (2013.01);
(Continued)

(58) Field of Classification Search
None
See application file for complete search history.

(56) References Cited

U.S. PATENT DOCUMENTS

| 5,129,400 A |   | 7/1992 | Makino et al. |
| 6,724,418 B1 | * | 4/2004 | Takahashi .............. A61B 1/042 348/61 |

(Continued)

FOREIGN PATENT DOCUMENTS

| CA | 2653228 A1 | 12/2007 |
| CN | 101784227 A | 7/2010 |

(Continued)

OTHER PUBLICATIONS

International Search Report and Written Opinion of PCT Application No. PCT/JP2018/015959, dated Jun. 19, 2018, 09 pages of ISRWO.

*Primary Examiner* — Dave Czekaj
*Assistant Examiner* — Samuel D Fereja
(74) *Attorney, Agent, or Firm* — Chip Law Group

(57) ABSTRACT

A control device according to an embodiment of the present technology includes an acquisition section, a block control section, and a calculator. The acquisition section acquires an image signal of a tissue of a living body irradiated with laser light and on which image-capturing has been performed. The block control section controls a size of a pixel block according to an image-capturing condition for the image-capturing on the tissue of a living body. The calculator calculates speckle data based on the acquired image signal, using the pixel block of which the size is controlled.

12 Claims, 16 Drawing Sheets

(51) Int. Cl.
    *A61B 1/06*     (2006.01)
    *A61B 5/026*    (2006.01)
    *G06T 7/00*     (2017.01)
    *H04N 5/235*    (2006.01)
    *H04N 5/225*    (2006.01)

(52) U.S. Cl.
    CPC ......... *G06T 7/0012* (2013.01); *H04N 5/2352* (2013.01); *H04N 5/232127* (2018.08); *G06T 2207/10056* (2013.01); *G06T 2207/10068* (2013.01); *G06T 2207/30104* (2013.01); *H04N 2005/2255* (2013.01)

(56) References Cited

U.S. PATENT DOCUMENTS

| | | |
|---|---|---|
| 2007/0276265 A1 | 11/2007 | Borgos |
| 2008/0071180 A1 | 3/2008 | Borgos |
| 2011/0013002 A1* | 1/2011 | Thompson ........... A61B 5/0261 348/77 |
| 2011/0176110 A1 | 7/2011 | Bublizt et al. |
| 2012/0277559 A1 | 11/2012 | Kohl-Bareis et al. |
| 2015/0323311 A1 | 11/2015 | Muijs et al. |
| 2017/0188853 A1* | 7/2017 | Nakao .................. A61B 5/0261 |
| 2019/0192048 A1* | 6/2019 | Making .................... G06T 1/00 |

FOREIGN PATENT DOCUMENTS

| | | |
|---|---|---|
| CN | 104620073 A | 5/2015 |
| CN | 106413543 A | 2/2017 |
| DE | 102008049846 A1 | 4/2010 |
| DE | 102008049881 A1 | 4/2010 |
| EP | 0392744 A1 | 10/1990 |
| JP | 02-268725 A | 11/1990 |
| JP | 2009-538210 A | 11/2009 |
| JP | 2010-117306 A | 5/2010 |
| JP | 2010-532699 A | 10/2010 |
| JP | 2012-503996 A | 2/2012 |
| JP | 2015-527096 A | 9/2015 |
| JP | 2016-005525 A | 1/2016 |
| JP | 2016-509509 A | 3/2016 |
| WO | 2007/140210 A2 | 12/2007 |
| WO | 2009/008745 A2 | 1/2009 |
| WO | 2010/037485 A1 | 4/2010 |
| WO | 2011/070357 A1 | 6/2011 |
| WO | 2013/185937 A1 | 12/2013 |
| WO | 2015/182065 A1 | 12/2015 |

* cited by examiner

Speckle Contrast (Cs) = Stdev($I_{m,n}$) / Ave($I_{m,n}$)

CONTROL DEVICE AND CONTROL METHOD

CROSS REFERENCE TO RELATED APPLICATIONS

This application is a U.S. National Phase of International Patent Application No. PCT/JP2018/015959 filed on Apr. 18, 2018, which claims priority benefit of Japanese Patent Application No. JP 2017-097151 filed in the Japan Patent Office on May 16, 2017. Each of the above-referenced applications is hereby incorporated herein by reference in its entirety.

TECHNICAL FIELD

The present technology relates to a control device, a control method, and a program that are applicable to, for example, an observation of a tissue of a living body.

BACKGROUND ART

In the past, a technology has been developed that irradiates laser light onto, for example, a tissue of a living body to detect a speckle pattern, and observes, for example, the tissue of a living body. For example, Patent Literature 1 discloses a spatial-domain diffuse speckle contrast analysis (sDSCA) system. In the sDSCA system, laser light irradiated inside a sample is scattered due to the movement of particles (blood flow) distributed within the sample, which results in creating a speckle pattern on the surface of the sample. An image of the speckle pattern is captured using a relay optical system oriented toward a specified position to perform image-capturing on the surface of the sample. A speckle contrast is calculated using the captured image, and, for example, the rate of blood flow through the sample is calculated (for example, paragraphs [0013], [0018], [0021], and [0027] of the specification, and FIG. 5 of Patent Literature 1).

CITATION LIST

Patent Literature

Patent Literature 1: Japanese Unexamined Patent Application Publication No. 2016-509509

DISCLOSURE OF INVENTION

Technical Problem

It is expected that, for example, the observation of a tissue of a living body based on a speckle pattern described above is applied to various scenes in, for example, surgery and a diagnosis related to internal medicine, and there is a need for a technology that makes it possible to provide a high degree of accuracy.

In view of the circumstances described above, it is an object of the present technology to provide a control device, a control method, and a program that make it possible to observe a tissue of a living body with a high degree of accuracy by optimally performing calculation processing, even if there is a change in an image-capturing condition of a camera.

Solution to Problem

In order to achieve the object described above, a control device according to an embodiment of the present technology includes an acquisition section, a block control section, and a calculator.

The acquisition section acquires an image signal of a tissue of a living body irradiated with laser light and on which image-capturing has been performed.

The block control section controls a size of a pixel block according to an image-capturing condition for the image-capturing on the tissue of a living body.

The calculator calculates speckle data based on the acquired image signal, using the pixel block of which the size is controlled.

In this control device, an image signal of a tissue of a living body irradiated with laser light and on which image-capturing has been performed, is acquired. A size of a pixel block is controlled according to an image-capturing condition for the image-capturing on the tissue of a living body, and speckle data is calculated from the image signal of the tissue of a living body using the pixel block. This makes it possible to calculate speckle data depending on an image-capturing condition, and to observe a tissue of a living body with a high degree of accuracy by optimally performing calculation processing, even if there is a change in an image-capturing condition of a camera.

The control device may further include a generator that generates an observation image of the tissue of a living body using the speckle data.

The speckle data may include a speckle contrast. In this case, the generator may generate the observation image using the speckle contrast.

This makes it possible to observe, for example, blood flow in a tissue of a living body with a high degree of accuracy using a speckle contrast.

The image-capturing condition may include at least one of a condition regarding an f-number (an aperture) of an imaging system that performs the image-capturing on the tissue of a living body, or a condition regarding an optical magnification of the imaging system.

This makes it possible to control a size of a pixel block as appropriate depending on a magnification or brightness that is applied when image-capturing is performed on a tissue of a living body, and to achieve an accurate observation.

The block control section may calculate a predicted speckle size using the image-capturing condition, and may control the size of the pixel block according to the calculated speckle size.

This makes it possible to control a size of a pixel block according to a speckle size, and to calculate desired speckle data.

The control device may further include a storage that stores therein a control table in which the image-capturing condition is associated with the size of the pixel block.

For example, the block control section can easily control a size of a pixel block using a control table, which results in being able to reduce, for example, a load to be imposed when performing processing.

The block control section may control the size of the pixel block such that a specified display parameter related to a display luminance of the observation image is kept substantially constant.

This makes it possible to, for example, observe a tissue of a living body while keeping, for example, brightness of the tissue of a living body substantially constant, the tissue of a living body being displayed on the observation image, and to observe the tissue of a living body with a high degree of accuracy.

The control device may further include a mode reception section that receives a selection of an image quality mode related to an image quality of the observation image. In this case, the block control section may control the size of the pixel block depending on the selected image quality mode.

For example, a speckle contrast is calculated depending on an image quality mode, and it becomes possible to generate an observation image with a desired image quality. This makes it possible to observe a tissue of a living body with a high degree of accuracy.

The mode reception section may receive an image quality mode related to a display resolution of the observation image.

This makes it possible to, for example, generate an observation image at the level of a display resolution depending on an image quality mode. This results in being able to observe a tissue of a living body with a high degree of accuracy.

The mode reception section may receive a plurality of image quality modes different from one another. In this case, the block control section may control the size of the pixel block such that the specified display parameter related to the display luminance of the observation image is kept substantially constant in ranges that are different with respect to respective image quality modes of the plurality of image quality modes.

This makes it possible to keep a display luminance of an observation image substantially constant in a range of, for example, a desired display resolution. This results in being able to observe a tissue of a living body with a sufficiently high degree of accuracy.

The plurality of image quality modes may include a first image quality mode and a second image quality mode, in which, from among the display luminance and the display resolution of the observation image, priority is given to the display luminance in the first image quality mode, and priority is given to the display resolution in the second image quality mode.

This makes it possible to, for example, switch between observation images that look different from each other as appropriate depending on, for example, the type of a tissue of a living body, and to improve the accuracy in observation.

The storage may store therein the control table in which a correspondence relationship among the image-capturing condition, the size of the pixel block, and the image quality mode related to an image quality of the observation image.

For example, the block control section can easily control a size of a pixel block corresponding to an image quality mode using a control table, which results in being able to improve a processing speed.

The control table may be generated using a specified target for correction.

This makes it possible to correct a control table properly, and to observe a tissue of a living body with a sufficiently high degree of accuracy.

The block control section may control the size of the pixel block depending on a size of a blood vessel in an image-capturing range of the tissue of a living body.

This makes it possible to, for example, generate an observation image with an image quality depending on a size of a blood vessel. This results in being able to reduce the burden on a user and to greatly improve an operation performance.

The control device may be configured as an endoscope or a microscope.

This makes is possible to improve the accuracy in an observation of a tissue of a living body using, for example, an endoscope or a microscope.

A control method according to an embodiment of the present technology is a control method that is performed by a computer system, and includes acquiring an image signal of a tissue of a living body irradiated with laser light and on which image-capturing has been performed.

A size of a pixel block is controlled according to an image-capturing condition for the image-capturing on the tissue of a living body.

Speckle data based on the acquired image signal is calculated using the pixel block of which the size is controlled.

A program according to an embodiment of the present technology causes a computer system to perform a process including:

acquiring an image signal of a tissue of a living body irradiated with laser light and on which image-capturing has been performed;

controlling a size of a pixel block according to an image-capturing condition for the image-capturing on the tissue of a living body; and calculating speckle data based on the acquired image signal, using the pixel block of which the size is controlled.

Advantageous Effects of Invention

As described above, the present technology makes it possible to observe a tissue of a living body with a high degree of accuracy by optimally performing calculation processing, even if there is a change in an image-capturing condition of a camera. Note that the effect described here is not necessarily limitative and may be any effect described in the present disclosure.

MODE(S) FOR CARRYING OUT THE INVENTION

Embodiments according to the present technology will now be described below with reference to the drawings.

[Observation System]

Figure 1:
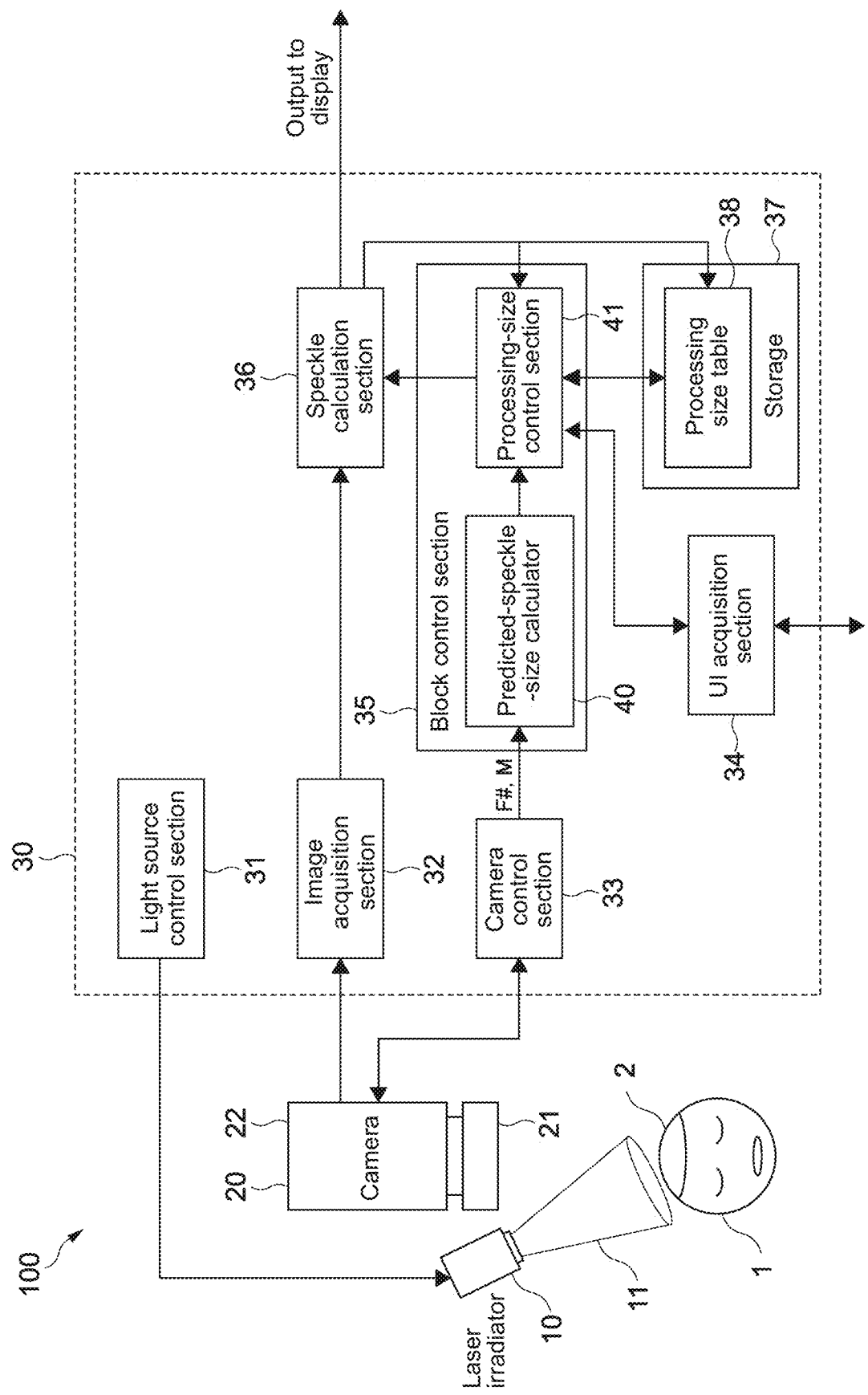
FIG. 1 is a block diagram of an example of a configuration of an observation system according to an embodiment of the present technology.

FIG. 1 is a block diagram of an example of a configuration of an observation system according to an embodiment of the present technology. For example, an observation system 100 is used to observe a field of operation in surgery, and to observe the inside of the body of a patient in a diagnosis related to internal medicine. Moreover, the present technology is applicable to an observation of any tissue of a living body.

The observation system 100 includes a laser irradiator 10, a camera 20, and a controller 30.

The laser irradiator 10 is arranged to be oriented toward an observation target site 2 of a patient 1, and irradiates laser light 11 onto the observation target site 2. The laser light 11 is scattered and reflected off the observation target site 2 onto which the laser light 11 is irradiated, and a light and dark spot pattern called a speckle is formed on the observation target site 2. FIG. 1 schematically illustrates the laser light 11 irradiated onto the head (the observation target site 2) of the patient 1. The observation target site 2 of the patient 1 corresponds to a tissue of a living body in the present embodiment.

The laser irradiator 10 is capable of irradiating the laser light 11 of a specified wavelength onto the entirety of the observation target site 2, the laser light 11 of a specified wavelength being generated using, for example, a laser light source that is not illustrated. Thus, a speckle pattern is formed over the entirety of the observation target site 2. The method for irradiating the laser light 11 or the like is not limited, and, for example, a beam expander that expands a light flux (beam) of the laser light 11, or a refractive lens that broadens an irradiation range may be used as appropriate.

The camera 20 includes a lens section 21 and an imaging section 22 that is connected to the lens section 21. The camera 20 is arranged such that the lens section 21 is oriented to the observation target site 2 of the patient 1, and captures an image of the observation target site 2 onto which the laser light 11 is irradiated.

The camera 20 is configured as, for example, a camera head unit (CHU), and connected to the controller 30 through, for example, a specified interface. In the present embodiment, the camera 20 corresponds to an imaging system.

The lens section 21 has an optical zoom function. The lens section 21 controls imaging parameters such as an f-number (an aperture) and an optical magnification to generate an optical image of the optically magnified or demagnified observation target site 2. A specific configuration for providing an optical zoom function is not limited, and, for example, an automatic zoom performed by an electronic control or a manual zoom may be performed as appropriate.

The imaging section 22 captures the optical image generated by the lens section 21, and generates an image signal of the observation target site 2. Here, an image signal is a signal that can form an image. For example, the image signal includes information such as a luminance value for each pixel. The type or the form of an image signal or the like is not limited, and an arbitrary form that makes it possible to form, for example, a moving image or a still image. An image sensor such as a complementary metal-oxide semiconductor (CMOS) sensor or a charge coupled device (CCD) sensor may be used as the imaging section 22.

The controller 30 includes hardware necessary for a configuration of a computer, such as a central processing unit (CPU), a read only memory (ROM), a random access memory (RAM), and a hard disk drive (HDD). In the present embodiment, the controller 30 corresponds to a control device.

Each functional block illustrated in FIG. 1 is provided by the CPU loading, into the RAM, a program according to the present technology that is stored in the ROM or the HDD. Then, a control method according to the present technology is performed by these functional blocks.

The program is installed on the controller 30 through, for example, various recording media. Alternatively, the program may be installed through, for example, the Internet.

A specific configuration of the controller 30 is not limited, and a device such as a field programmable gate array (FPGA), an image processing integrated circuit (IC), or other application specific integrated circuits (ASICs) may be used.

As illustrated in FIG. 1, the controller 30 includes, as a functional block, a light source control section 31, an image acquisition section 32, a camera control section 33, a UI acquisition section 34, a block control section 35, and a speckle calculation section 36. Further, a processing size table 38 is stored in a storage 37 that is constituted of, for example, the ROM of the controller 30. Note that dedicated hardware may be used as appropriate in order to provide the respective functional blocks.

The light source control section 31 controls, for example, an irradiation intensity of the laser light 11 irradiated by the laser irradiator 10. For example, the light source control section 31 acquires information regarding an irradiation intensity of the laser light 11 that is designated by an operator who operates the observation system 100. The light source control section 31 outputs an instruction to output, to the laser irradiator 10, the laser light 11 of the designated irradiation intensity. This makes it possible to irradiate the laser light 11 of an irradiation intensity desired by an operator.

The method for controlling an irradiation intensity of the laser light 11 or the like is not limited. For example, the irradiation intensity of the laser light 11 may be controlled as appropriate according to, for example, an exposure time of the camera 20. Note that not only the irradiation intensity of the laser light 11, but also arbitrary parameters such as a wavelength and an irradiation range of the laser light 11 may be controlled as appropriate by the light source control section 31.

The image acquisition section 32 acquires an image signal generated by the camera 20. In other words, the image acquisition section 32 acquires an image signal of the observation target site 2, in which the laser light 11 is irradiated onto the observation target site 2 and image-capturing is performed on the observation target site 2. The image signal acquired by the image acquisition section 32 is output to the speckle calculation section 36. In the present embodiment, the image acquisition section 32 corresponds to an acquisition section.

The camera control section 33 is connected to the camera 20 through, for example, an interface, and controls an operation of the camera 20. For example, the camera control section 33 outputs, to the camera 20, a signal that specifies, for example, a zoom amount (an optical magnification), a stop, or an exposure time of the camera 20. The camera 20 captures an image of the observation target site 2 according to the signal output by the camera control section 33. This makes it possible to electronically control an operation of the camera 20.

Further, the camera control section 33 acquires an imaging parameter for performing image-capturing on the observation target site 2. Examples of the imaging parameter include, for example, an f-number (an aperture) and an optical magnification of the lens section 21 (the camera 20). The image parameter acquired by the camera control section 33 is output to the block control section 35 by the camera control section 33. In the present embodiment, the imaging parameter corresponds to an image-capturing condition.

For example, a manual zoom in which, for example, a zoom amount or a stop of the lens section 21 is directly changed by an operator, may be performed. In this case, the camera control section 33 acquires an imaging parameter such as an optical magnification or a stop after the change. The timing at which an imaging parameter is acquired or the like is not limited, and, for example, the imaging parameter of the camera 20 may be constantly monitored by the camera control section 33.

The UI acquisition section 34 acquires, for example, an instruction input by an operator through a user interface (UI) that is not illustrated. A display device such as a display and an input device such as a mouse and a keyboard are used as the user interface as appropriate. For example, the operator inputs an instruction using an input device while viewing an operation screen displayed on a display device. The type of a user interface or the like is not limited, and, for example, a display provided with a touch sensor, a foot switch, or a control switch used by hand may be used.

In the present embodiment, the UI acquisition section 34 receives a selection of an image quality mode related to an image quality of an observation image described later. In other words, the UI acquisition section 34 acquires information regarding which image quality mode is selected (for which image quality mode an instruction is given) by an operator. The instruction on an image quality mode acquired by the UI acquisition section 34 is output to the block control section 35. In the present embodiment, the UI acquisition section 34 serves as a mode reception section.

Note that the content of the instruction acquired by the UI acquisition section 34 or the like is not limited. For example, an instruction on the irradiation intensity of the laser irradiator 10 described above, or an instruction on the optical magnification of the camera 20 may be acquired as appropriate. Moreover, various instructions on the observation system 100 may be acquired by the UI acquisition section 34.

The block control section 35 includes a predicted-speckle-size calculator 40 and a processing-size control section 41. The predicted-speckle-size calculator 40 calculates a speckle size using an imaging parameter input by the camera control section 33.

The speckle size is a size of each spot forming a speckle. In general, the speckle size varies depending on an imaging system that captures an image of a speckle pattern. For example, a speckle size d is obtained using the following formula.

$$d = F\# \times (1+M) \times \lambda \times 1.22$$

Here, F # represents an f-number of the lens section 21, and M represents an optical magnification M of the lens section 21. Further, λ represents a wavelength of the irradiated laser light 11. This formula may be hereinafter referred to as a speckle size calculating formula.

Figure 13A:
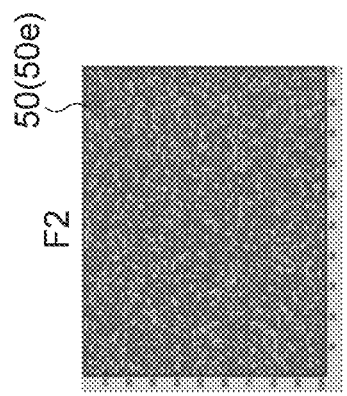
FIGS. 13A and 13B is a are diagrams illustrating a relationship between a speckle size and an imaging parameter.
Figure 13A:
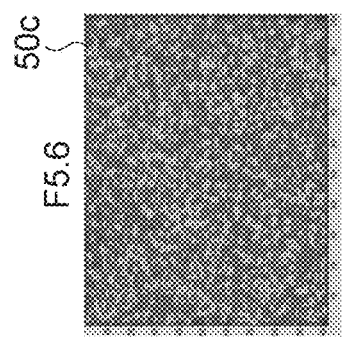
Figure 13A:
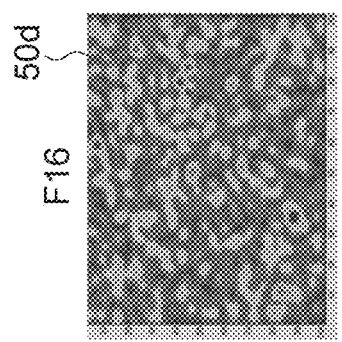
Figure 13B:
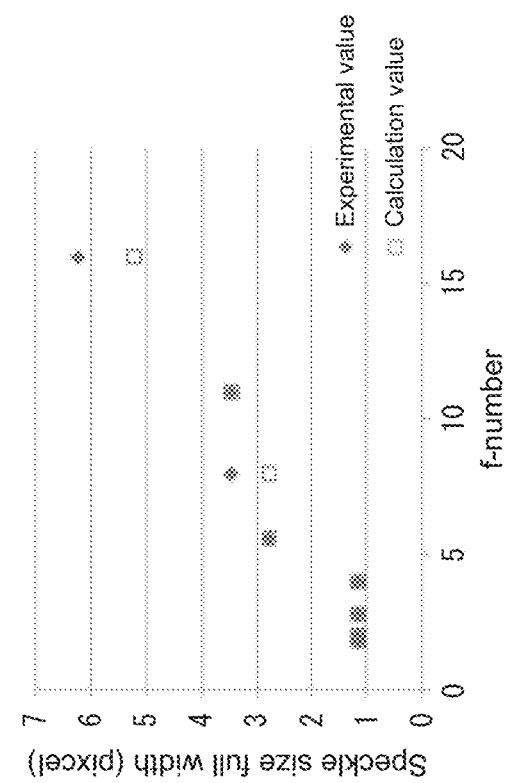

In the present embodiment, the speckle size d is calculated by the predicted-speckle-size calculator 40 using the speckle size calculating formula, by use of the f-number F # and the optical magnification M included in the imaging parameter. Thus, the predicted-speckle-size calculator 40 can calculate the speckle size d in a speckle pattern of which an image is captured. The calculated speckle size d is output to the processing-size control section 41. The calculated speckle size is a predicted value, but it has been confirmed to be nearly in agreement with an actually measured value, as illustrated in FIGS. 13A and 13B.

Note that the method for calculating a speckle size d using an imaging parameter or the like is not limited, and the speckle size d may be calculated by other methods. For example, the speckle size d may be calculated by indicating an f-number F # using a focal length, by use of an aperture size at a position of a stop of the lens section 21. Moreover, an arbitrary method that makes it possible to calculate a speckle size d may be used.

The processing-size control section 41 controls the size of a cell that is a pixel block (cell size). The cell is, for example, a rectangular block constituted of m×n pixels, and is used when a speckle contrast is calculated using an image signal. The number of pixels of (width×height) (m×n) corresponds to a cell size. The shape of a cell or the like is not limited, and, for example, a cell having an arbitrary shape may be used. The cell and the speckle contrast will be described in detail later.

The processing-size control section 41 controls a cell size using the speckle size d calculated by the predicted-speckle-size calculator 40. Further, the processing-size control section 41 controls the cell size according to an image quality mode acquired by the UI acquisition section 34. Thus, the cell size controlled by the processing-size control section 41 is a size depending on the speckle size d and the image quality mode.

In the present embodiment, the processing size table 38 stored in the storage 37 is used when a size of a cell is controlled. A correspondence relationship among a speckle size d, an image quality mode, and a size of a cell is recorded in the processing size table 38. For example, the processing-size control section 41 acquires, from the processing size table 38, a value of a size of a cell that corresponds to a calculated speckle size d and a designated image quality mode. This makes it possible to easily control the size of a cell. In the present embodiment, the processing size table 38 corresponds to a control table.

As described above, the block control section 35 calculates a speckle size using an imaging parameter, and controls a cell size using the calculated speckle size. In other words, the block control section 35 controls the size of a cell using an imaging parameter for performing image-capturing on the observation target site 2.

The speckle calculation section 36 calculates speckle data using the image signal acquired by the image acquisition section 32, by use of a cell of which the size is controlled by the processing-size control section 41 (the block control section 35). Here, the speckle data is data regarding a speckle pattern of the observation target site 2. The speckle data is calculated by performing processing, as appropriate, on information regarding, for example, luminance values of respective pixels included in the image signal.

In the present embodiment, a speckle contrast is calculated by the speckle calculation section 36 as speckle data. Note that not only a speckle contrast, but also, for example, an average, a variance, and a standard deviation of a luminance value in a speckle pattern may be calculated as the speckle data. The calculated speckle data can be output to the processing-size control section 41 and the processing size table 38, and is used to, for example, correct the processing size table 38.

Further, an observation image of the observation target site 2 is generated by the speckle calculation section 36 according to the calculated speckle contrast. The generated observation image is output to a display device such as a display that is not illustrated. In the present embodiment, the speckle calculation section 36 serves as a calculator and a generator.

Figure 2:
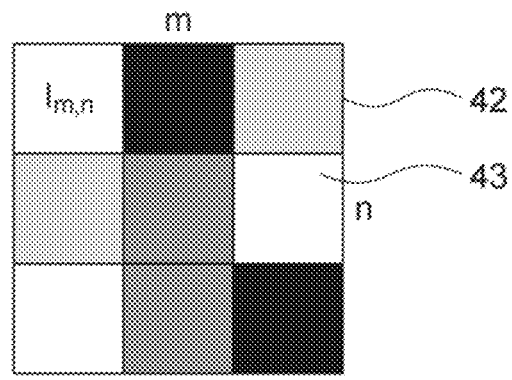
FIG. 2 is a schematic diagram for explaining an example of calculating a speckle contrast.
Figure 3A:
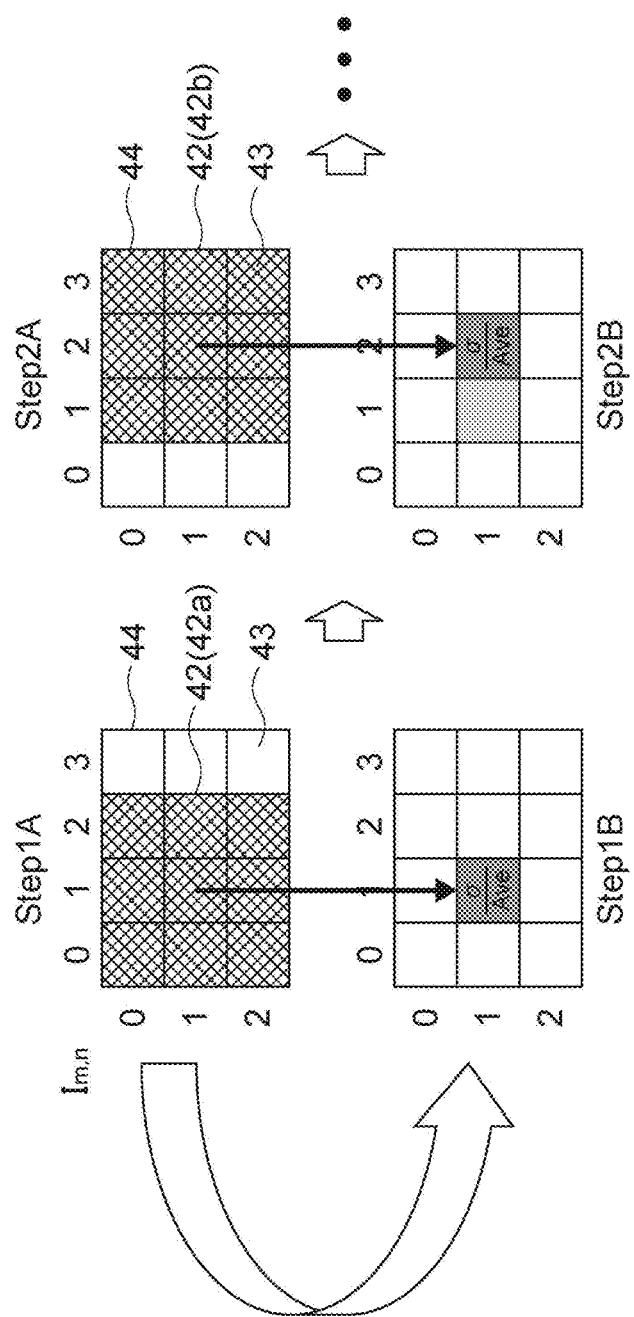
FIGS. 3A and 3B is a are schematic diagrams for explaining an example of calculating a speckle contrast.
Figure 3B:
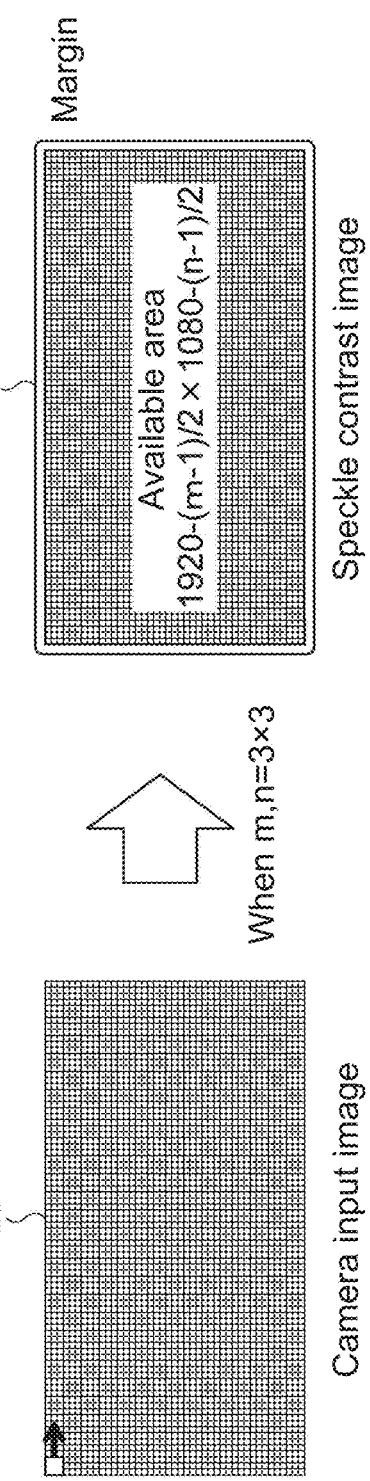

FIGS. 2, 3A, and 3B are schematic diagrams for explaining an example of calculating a speckle contrast. FIG. 2 schematically illustrates, using lightness and darkness, a luminance value of a pixel 143 included in a 3×3 cell 42.

As illustrated in FIG. 2, a speckle contrast Cs is obtained using the following formula, by use of a standard deviation $\sigma$ and an average A of luminance values I(m,n) of the respective pixels 43 included in the cell 42.

$$Cs = \sigma/A$$

Further, the standard deviation $\sigma$ and the average A of the luminance value I(m,n) are obtained using the following formulas.

$$A = \text{Ave}(I(m,n)) = \Sigma[I(m,n)]/N$$

$$\sigma = \text{Stdev}(I(m,n)) = \text{Sqrt}((\Sigma[I(m,n)-\text{Ave}]^2)/N)$$

Here, the summation symbol $\Sigma$ represents a sum regarding luminance values of all of the pixels 43 in the cell 42. Further, N represents a total number of pixels 43 included in the cell 42, where N=3×3=9 in FIG. 2. Note that the method for calculating a speckle contrast Cs is not limited, and, for example, a variance $\sigma^2$ of the luminance value I(m,n) or the like may be used instead of the standard deviation G. Further, a difference $(I_{max}(m,n)-I_{min}(m,n))$ between a maximum value and a minimum value of the luminance value I(m,n) in the cell 42 may be used as the speckle contrast Cs.

FIG. 3A illustrates an example of a process of calculating a speckle contrast Cs using a 3×3 cell 42. For example, as illustrated in FIGS. 3A and 3B, the position of a pixel 43 situated on an upper left corner of an image 44 is set to be a coordinate (0,0). First, the speckle calculation section 36 sets a cell 42a that includes the pixel 43 situated on the upper left corner. In this case, the cell 42a having, in its center, a pixel 43 situated at a coordinate (1,1), is set (Step 1A).

The speckle calculation section 36 calculates a speckle contrast Cs(1,1) with respect to the cell 42a having the coordinate (1,1) in its center. In other words, Cs(1,1) is calculated using luminance values of the central pixel 43 and eight pixels 43 situated around the central pixel 43. The calculated speckle contrast Cs(1,1) is recorded as a speckle contrast Cs that corresponds to the pixel 43 situated at the coordinate (1,1) (Step 1B).

Next, the speckle calculation section 36 sets a cell 42b having a coordinate (2,1) in its center, the coordinate (2,1) being situated at a position displaced to the right from the coordinate (1,1) by one pixel (Step 2A). The speckle calculation section 36 calculates a speckle contrast Cs(2,1) with respect to the cell 42b, and records the calculated speckle contrast Cs(2,1) as a speckle contrast Cs of a pixel 43 situated at the coordinate (2,1) (Step 2B).

As described above, the process of calculating a speckle contrast Cs of a pixel 43 situated in the center of a cell 42 is performed every time the center of the cell 42 is displaced by one pixel. Consequently, speckle contrasts Cs corresponding to respective pixels 43 included in an image signal are sequentially calculated.

Note that the method for calculating a speckle contrast Cs using a cell 42 or the like is not limited. For example, a calculated speckle contrast Cs may be assigned to another pixel 43 different from a central pixel 43 situated in a cell 42. Further, the amount, the direction, the order of displacing a cell 42, and the like are not limited, and, for example, they may be changed according to, for example, a processing time necessary for image processing.

FIG. 3B schematically illustrates the entirety of the process of calculating a speckle contrast Cs. The diagram on the left in FIG. 3B is a schematic diagram of an image captured by the camera 20 (a camera input image 50). The speckle calculation section 36 starts performing the process of calculating a speckle contrast Cs from an upper left corner of the camera input image 50. An original image used to calculate a speckle contrast Cs, that is, the camera input image 50 will be hereinafter referred to as a speckle image 50.

According to the calculated speckle contrast Cs, the speckle calculation section 36 generates a speckle contrast image 60 that is an observation image. The diagram on the right in FIG. 3B is a schematic diagram of the speckle contrast image 60.

The speckle contrast image 60 is generated by converting a value of a speckle contrast Cs into a luminance value. For example, a high-luminance value is set for a pixel having a high speckle contrast Cs, and a low-luminance value is set for a pixel having a low Cs. The method for converting a speckle contrast Cs into a luminance value or the like is not limited, and any method may be used. For example, a luminance value in which high luminance and low luminance are inversely assigned to high and low speckle contrasts Cs, may be set.

Note that it is not possible to set a cell 42 with respect to a pixel situated on the periphery of an original image (the speckle image 50). Thus, in the speckle contrast image 60, a range of a pixel 43 that is used for display (available area) is smaller than that in the speckle image 50. For example, when the size of the speckle image 50 is 1920×1080 (full-HD), the available area of the speckle contrast image 60 is obtained using the following formula.

$$\text{Available area} = (1920-(m-1)/2) \times (1080-(n-1)/2)$$

With respect to a pixel 43 situated on the periphery for which a speckle contrast Cs is not calculated, a specified luminance value is set and used as a margin.

Figure 4:
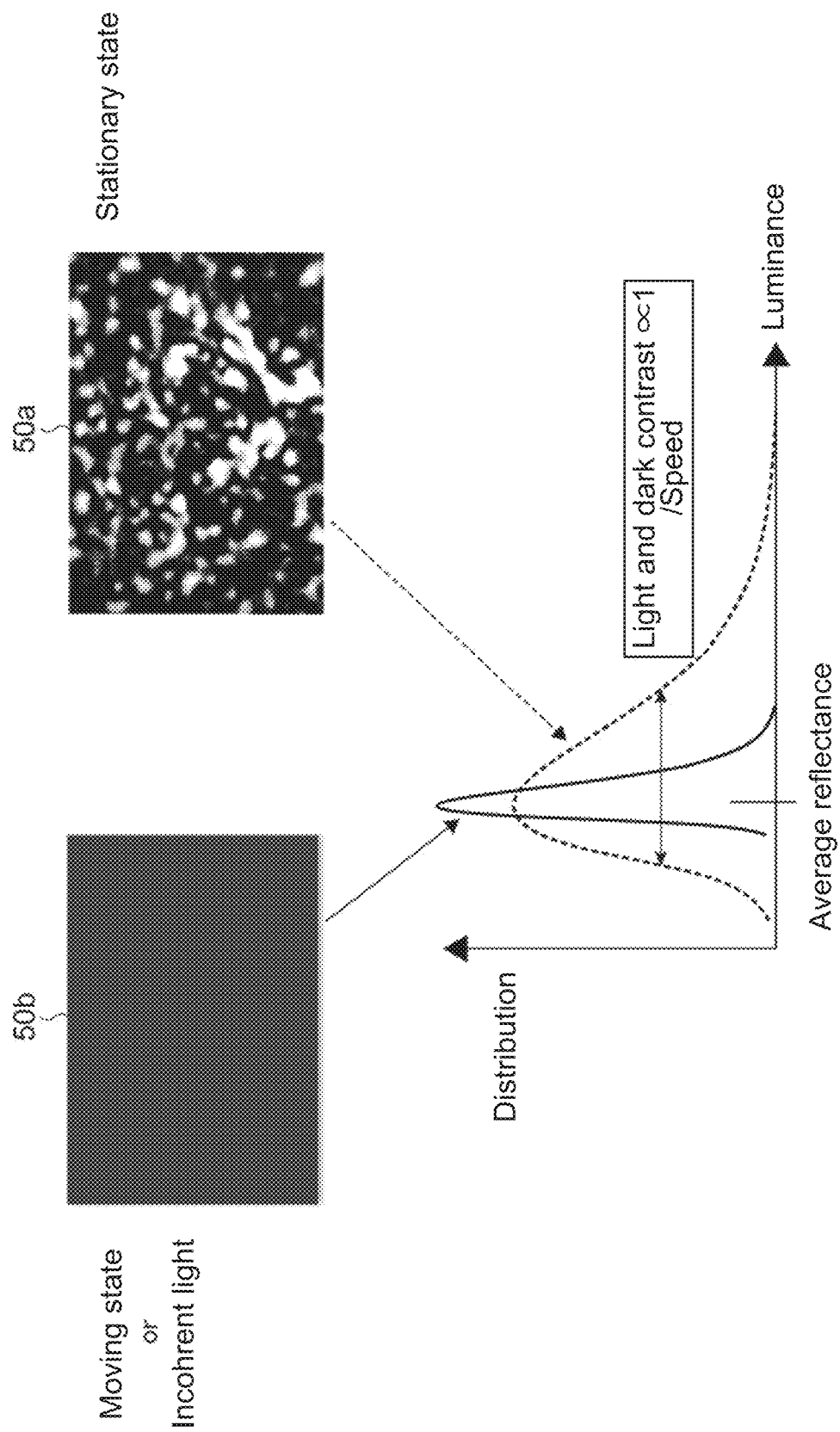
FIG. 4 is a schematic diagram for explaining the characteristics of a speckle pattern.

FIG. 4 is a diagram for explaining the characteristics of a speckle pattern. An image illustrated on the upper right of FIG. 4 is a raw image (a speckle image 50a) of an observation target in a stationary state, in which the laser light 11 is irradiated onto the observation target in a stationary state and the raw image is captured. Further, an image illustrated on the upper left is a raw image (a speckle image 50b) of the observation target in a moving state, in which the laser light 11 is irradiated onto the observation target in a moving state and the raw image is captured.

In general, when highly coherent light such as the laser light 11 is irradiated onto an observation target, the phase of the laser light 11 (reflection light) reflected off the observation target is changed at random. Pieces of laser light 11 whose respective phases are randomly different interfere with one another so that a light and dark speckle pattern is formed. For example, when an observation target is in a stationary state, the position at which interference occurs or the like becomes stable, which results in forming a clear speckle pattern as shown in the speckle image 50a on the right.

On the other hand, when the laser light 11 is irradiated onto a moving target, there is a change in, for example, the position at which interference occurs, a light and dark pattern of a speckle pattern is changed, and the patterns are integrated during an exposure time. This results in a decrease in a light and dark contrast (the speckle image 50b on the left). The level of a decrease in a light and dark contrast is represented by, for example, a value depending on an amount of the movement of the camera 20 during an exposure time. In other words, the decrease in a light and dark contrast is an indicator in which a speed is reflected.

In the lower portion of FIG. 4, there is a graph showing luminance distributions of the speckle image 50a in a stationary state and the speckle image 50b in a moving state. The horizontal axis of the graph represents a luminance value, and its vertical axis represents the number of pixels (a distribution) for each luminance value. The luminance distributions of the speckle image 50a in a stationary state and the speckle image 50b in a moving state are respectively represented by a dotted line and a solid line.

As shown in the graph, when an observation target is in a stationary state, the luminance distribution is larger in width compared to the case of a moving state. In other words, in the speckle image 50a in a stationary state, there is a large difference in luminance between a light pixel and a dark pixel, and the speckle image 50a in a stationary state is an image with a high light and dark contrast. On the other hand, in the speckle image 50b in a moving state, there is a small difference in luminance between a light pixel and a dark pixel, and the speckle image 50b in a moving state is an image with a low light and dark contrast.

The width of the luminance distribution (light and dark contrast) is substantially proportional to an amount of a movement during an exposure time, that is, to the inverse of a speed of the movement. More precisely, the speckle contrast Cs is represented using the following relationship.

$$Cs=(\beta \times (\exp(-2X-1+2X))/(2X^2))^{(1/2)}$$

Here, $\beta$, represents a normalization factor, and X is represented as $X=T/\tau$ using an exposure time T and a correlation time $\tau$. Note that the correlation time $\tau$ is inversely proportional ($\tau \propto 1/v$) to an average speed v of blood flow.

Thus, in a speckle image, a light and dark contrast is decreased as the movement speed in an observation target becomes higher. For example, the width of a luminance distribution of a site with blood flow in, for example, a tissue of a living body, corresponds to a speed of the blood flow. Further, it is also possible to represent a speed of blood flow using a speckle contrast calculated using a standard deviation of a luminance distribution.

Note that the average luminance (average reflectance) of the laser light 11 reflected off an observation target is substantially the same when the observation target is in a moving state and in a stationary state. Thus, the luminance distributions in the respective states are each centered on substantially the same luminance value (average reflectance).

Figure 5:
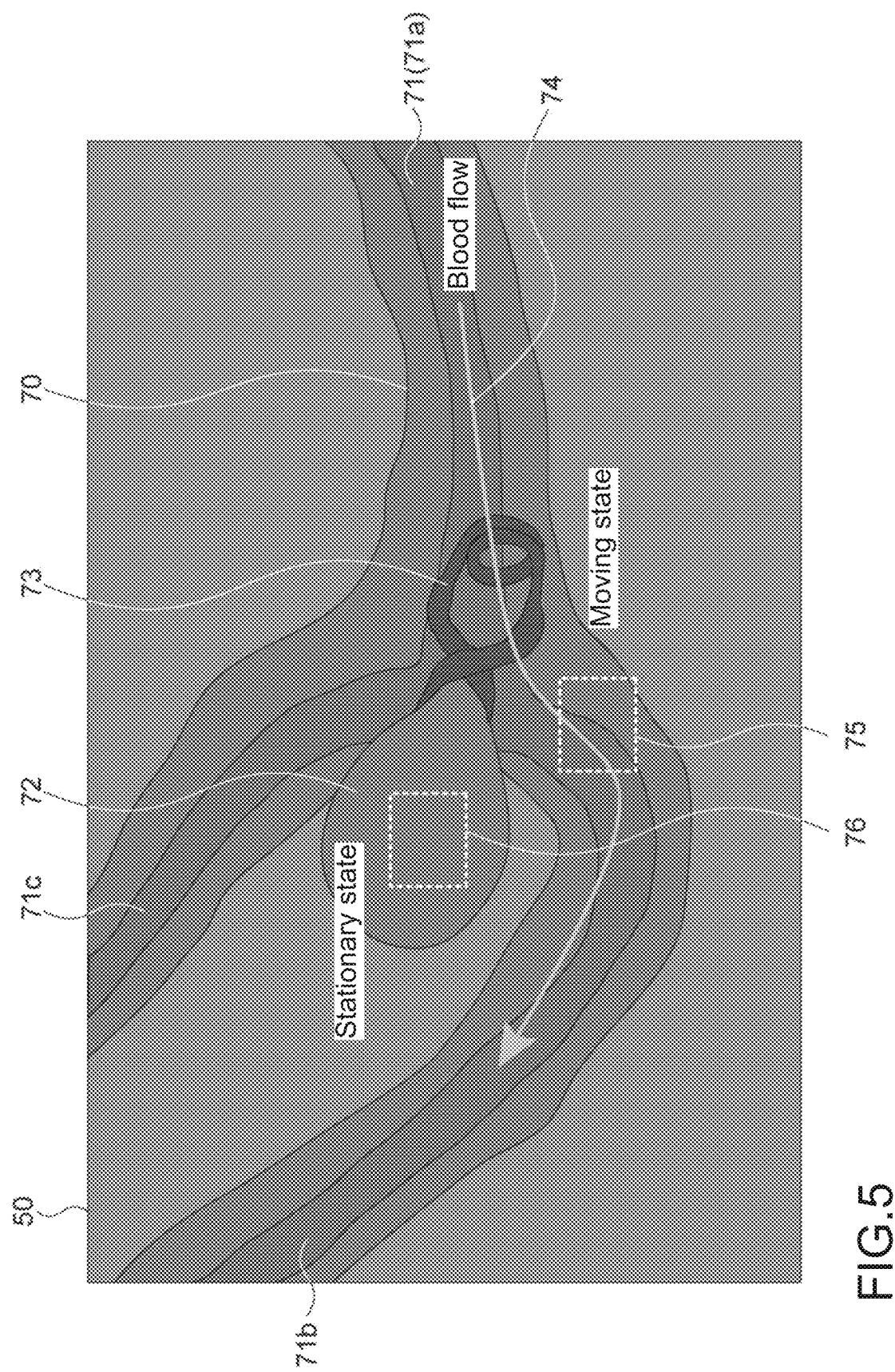
FIG. 5 schematically illustrates an example of a speckle image.

FIG. 5 schematically illustrates an example of a speckle image. FIG. 5 schematically illustrates the speckle image 50 of a blood vessel phantom 70, in which the laser light is irradiated onto the blood vessel phantom 70 and the speckle image 50 is captured. Note that, in FIG. 5, a site of the blood vessel phantom, in which the blood flow is fast, and a site of the blood vessel phantom, in which the blood flow is low, are represented using different colors.

In the blood vessel phantom 70, a blood vessel 71a on the right is separated into an upper blood vessel 71b and a lower blood vessel 71c at a separation point situated at the center of the image. An aneurysm 72 is formed at the separation point, and blood flow 74 to the aneurysm 72 is shut off using a blood vessel clip 73. Note that FIG. 5 schematically illustrates the blood flow 74 from the right to the left. Blood is pooled inside the aneurysm 72.

Figure 6:
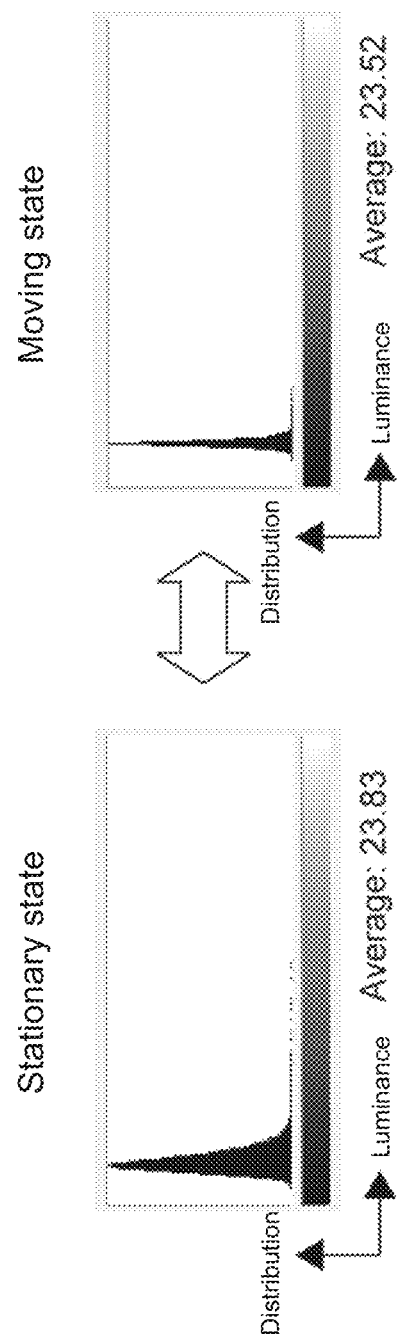
FIG. 6 is a diagram including graphs of luminance distributions of the speckle image illustrated in FIG. 5.

FIG. 6 is a diagram including graphs of luminance distributions of the speckle image 50 illustrated in FIG. 5. The graph on the right in FIG. 6 shows a luminance distribution in a blood vessel (the lower blood vessel 71b) through which blood is flowing, and the graph on the left in FIG. 6 shows a luminance distribution in the aneurysm 72. The graphs respectively provide a result regarding a luminance distribution in a portion region 75 on the lower blood vessel 71b, and a result regarding a luminance distribution in a portion region 76 on the aneurysm 72.

The lower blood vessel 71b is in a moving state since blood moves inside the lower blood vessel 71b. Thus, as shown in the graph on the right in FIG. 6, the luminance distribution in the lower blood vessel 71b has a small width, and thus the light and dark contrast is suppressed. On the other hand, the aneurysm 72 is in a stationary state in which blood is pooled. Thus, as shown in the graph on the left in FIG. 6, the luminance distribution in the aneurysm 72 has a large width, and thus the light and dark contrast becomes higher.

Note that the lower blood vessel 71b and the aneurysm 72 are made of the same material, and the value of the average luminance (23.52) in the lower blood vessel 71b and the value of the average luminance (23.82) in the aneurysm 72 are substantially the same. As described above, a site in a moving state and a site in a stationary state have a similar average luminance, but there is a difference between them in luminance distribution, that is, in light and dark contrast.

Figure 7A:
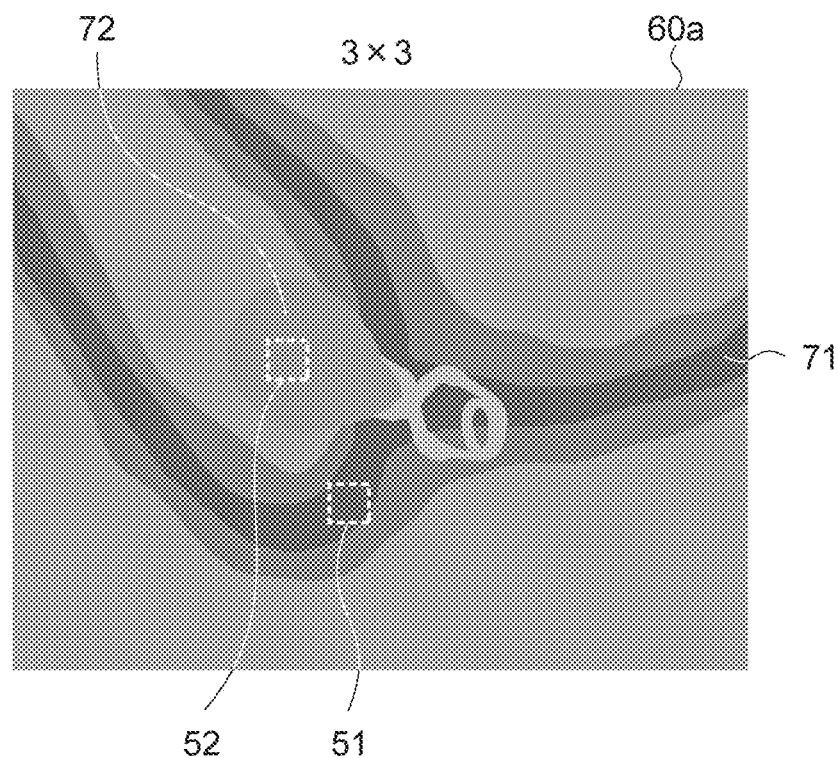
FIGS. 7A and 7B is a are schematic diagrams illustrating examples of speckle contrast images.
Figure 7B:
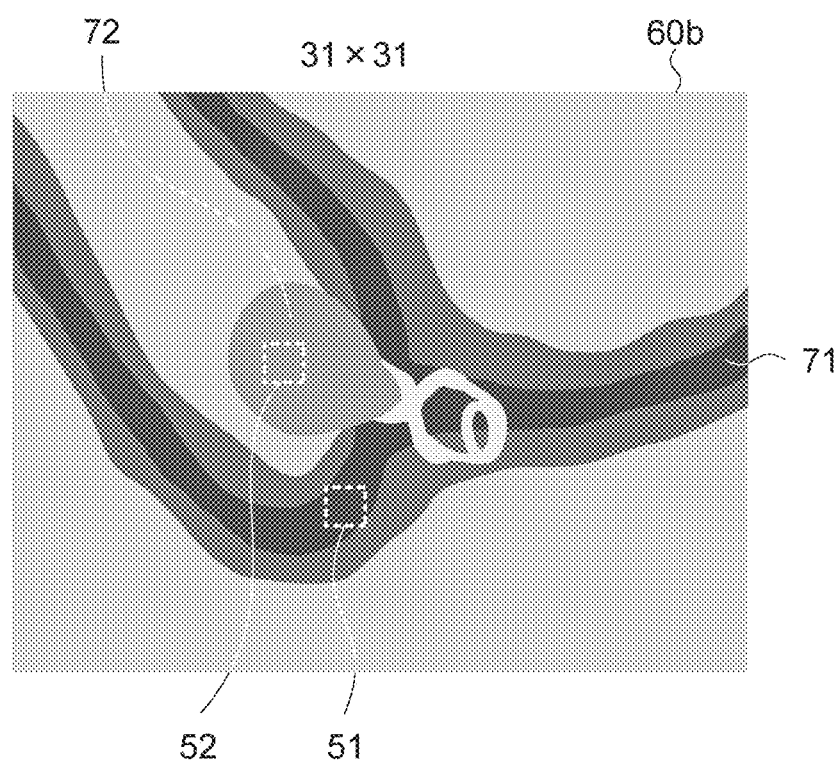

FIGS. 7A and 7B are schematic diagrams illustrating examples of speckle contrast images. FIG. 7A schematically illustrates a speckle contrast image 60a generated using a 3×3 cell 42. The speckle contrast image 60a is generated, for example, using the speckle image 50 described in, for example, FIG. 5 as a raw image.

In the speckle contrast image 60a, the luminance of a portion through which blood is flowing, that is, the luminance of the inside of the blood vessel 71, is low, and the luminance of a portion in which blood is pooled, that is, the luminance of the aneurysm 72, is higher than that in the blood flowing portion. Thus, the blood vessel 71 (the blood flowing portion) and the aneurysm 72 (the blood pooling portion) are displayed at different brightnesses. Of course, the speckle contrast image 60a in which a high luminance and a low luminance are inversely assigned, may be generated, where the blood vessel 71 is displayed brightly, and the aneurysm 72 is displayed darkly.

As described above, the value of a speckle contrast Cs is a value proportional to a standard deviation $\sigma$ of luminance values I(m,n) of respective pixels 43 included in a cell 42. For example, regarding a region in which the luminance distribution has a large width, the standard deviation σ of a luminance value I(m,n) is large, and the value of a speckle contrast Cs is also large. Conversely, regarding a region in which the luminance distribution has a small width, the value of a speckle contrast Cs is also small.

As described above, a speckle contrast Cs is calculated for each pixel 43 depending on the light and dark contrast (the width of a luminance distribution) around the pixel 43. The speckle contrast image 60*a* is generated by converting the calculated speckle contrast Cs into a luminance value. Thus, the brightness (the luminance value) of each pixel 43 of the speckle contrast image 60*a* has a value depending on the light and dark contrast around the pixel 43.

This results in, for example, displaying a site with a high light and dark contrast (a site in which a speckle is clear) and a site with a low light and dark contrast (a site in which there is a difficulty in recognizing a speckle) at brightnesses different from each other. In other words, it becomes possible to visually represent, in the speckle contrast image 60*a*, the blood vessel 71 in a moving state and the aneurysm 72 in a stationary state using the difference in brightness between them.

FIG. 7B schematically illustrates a speckle contrast image 60*b* generated using a 31×31 cell 42. If the size of the cell 42 is made larger, values of a speckle contrast Cs that are calculated for respective pixels are smoothed.

For example, regarding the blood vessel 71 (blood flowing portion), substantially the same value is calculated with respect to speckle contrasts Cs of respective pixels 43. Likewise, also regarding the aneurysm 72 (pooling portion), substantially the same value is calculated with respect to speckle contrasts Cs of respective pixels 43. Thus, compared to the speckle contrast image 60*a* situated on the left, the blood vessel 71 and the aneurysm 72 are each displayed at a substantially uniform brightness.

Figure 8:
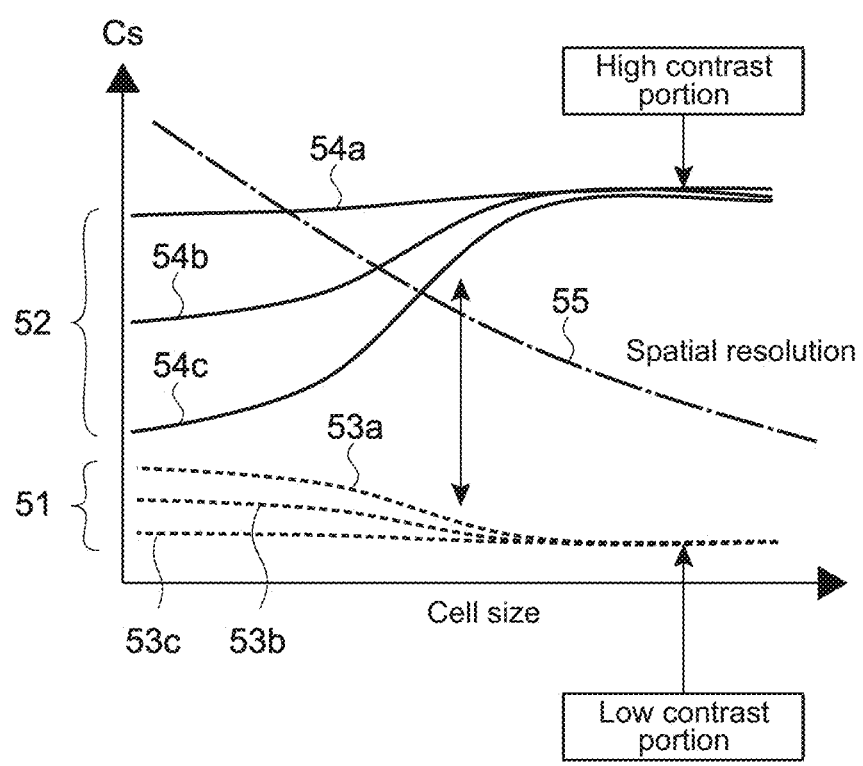
FIG. 8 is a graph illustrating a relationship between a cell size and a speckle contrast.

FIG. 8 is a graph illustrating a relationship between a cell size and a speckle contrast. The graph illustrated in FIG. 8 schematically represents a relationship between a cell size and the value of a speckle contrast Cs that is calculated for the cell size. The site in a moving state (the blood vessel 71) with a low light and dark contrast in the speckle image 50 will be hereinafter referred to as a low contrast portion 51. Further, the site in a stationary state (the aneurysm 72) with a high light and dark contrast will be hereinafter referred to as a high contrast portion 52.

The graph represented by a dotted line includes a maximum value 53*a*, an average value 53*b*, and a minimum value 53*c* of a speckle contrast Cs calculated for the low contrast portion 51. Further, the graph represented by a solid line includes a maximum value 54*a*, an average value 54*b*, and a minimum value 54*c* of a speckle contrast Cs calculated for the high contrast portion 52. Note that the graph illustrated in FIG. 8 schematically illustrates a spatial resolution 55 of the speckle contrast image depending on a cell size, using a dot-dash line.

As illustrated in the graph of FIG. 8, when the cell size is small, the space between the maximum value 54*a* and the minimum value 54*b* of the high contrast portion 52 is wide, and values of various speckle contrasts Cs are calculated. As the cell size becomes larger, the maximum value 54*a* increases gradually. The minimum value 54*b* increases to be closer to the maximum value 54*a*, and then the space between the minimum value 54*b* and the maximum value 54*a* becomes smaller. Thus, with an increase in a cell size, the value of a speckle contrast Cs calculated for the high contrast portion 52 converges to a value closer to the maximum value 54*a*.

Consequently, in the speckle contrast image 60*b* calculated in a large cell size, luminance values of respective pixels included in the high contrast portion 52 are close to one another, and thus the entirety of the high contrast portion 52 is displayed at the same brightness. Further, the luminance value of the high contrast portion 52 increases as the cell size becomes larger. The luminance value of the high contrast portion 52 represents a brightness of the entirety of the high contrast portion 52, and is, for example, an average of luminance values of respective pixels included in the high contrast portion 52.

In the low contrast portion 51, as the cell size becomes larger, the maximum value 53*a* decreases to be closer to the minimum value 53*b*. Thus, with an increase in a cell size, the value of a speckle contrast Cs calculated for the low contrast portion 51 converges to a value closer to the minimum value 53*b*. Consequently, the luminance value of the low contrast portion 51 of the speckle contrast image 60*b* (for example, an average of luminance values of respective pixels) decreases as the cell size becomes larger.

As described above, in the speckle contrast image 60, the blood flowing portion (the low contrast portion 51) and the blood-flow pooling portion (the high contrast portion 52) are more likely to be substantially uniformly displayed at respective brightnesses if the cell size is larger. Consequently, a portion with blood flow is a uniformly dark region, and a portion with lower blood flow is displayed as a uniformly bright region. This makes it possible to, for example, easily recognize, for example, the presence or absence of blood flow.

Note that, with an increase in a cell size, the value of a speckle contrast Cs is further smoothed, and the spatial resolution 55 of the speckle contrast image 60 is reduced. For example, regarding the speckle contrast images 60*a* and 60*b* illustrated in FIGS. 7A and 7B, the spatial resolution 55 of the image 60*a* generated in a small cell size (3×3) is higher. As described above, in the speckle contrast image 60, there is a trade-off relationship between a contrast and the spatial resolution 55.

Figure 9A:
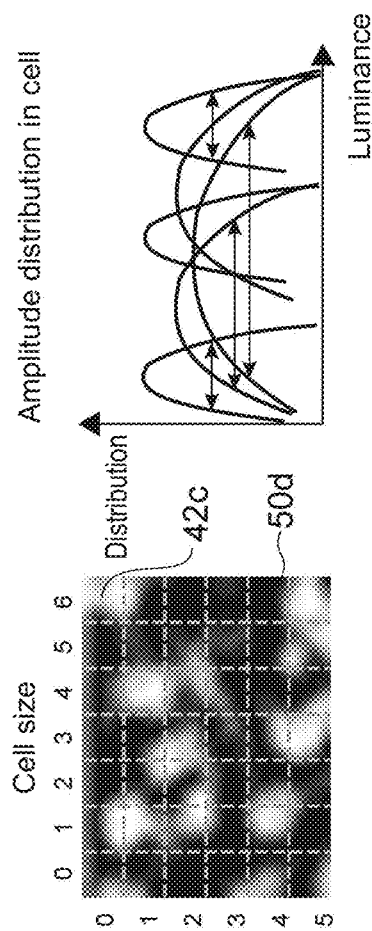
FIGS. 9A, 9B, and 9C is a are schematic diagrams for explaining a relationship between a cell size and a speckle contrast.
Figure 9B:
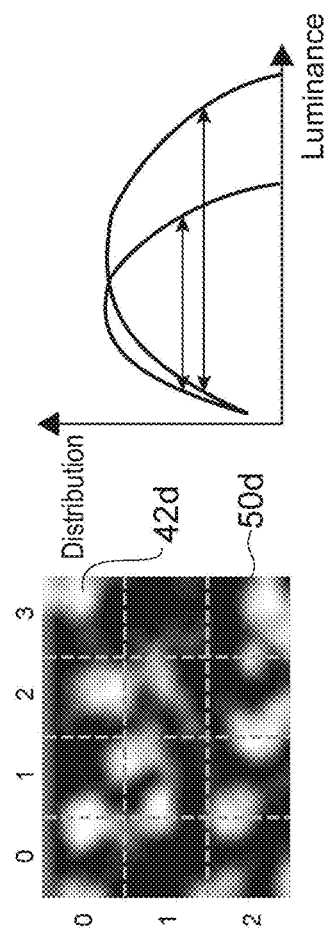
Figure 9C:
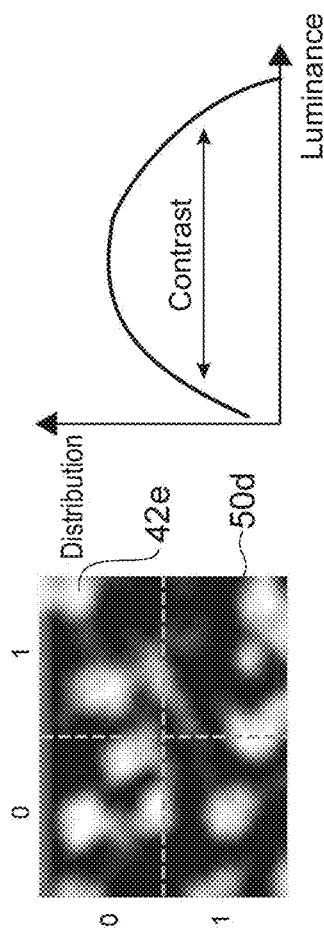
Figure 10A:
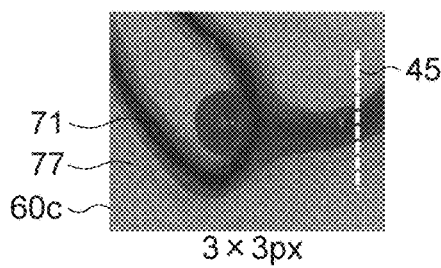
FIGS. 10A, 10B, 10C, 10D, 10E, and 10F is a are diagrams for explaining a relationship between a cell size and a speckle contrast image.
Figure 10A:
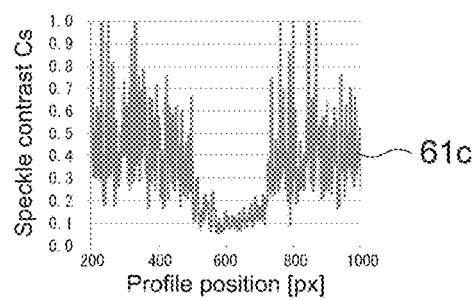
Figure 10B:
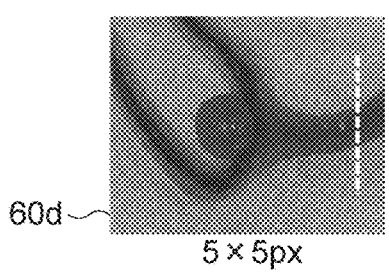
Figure 10B:
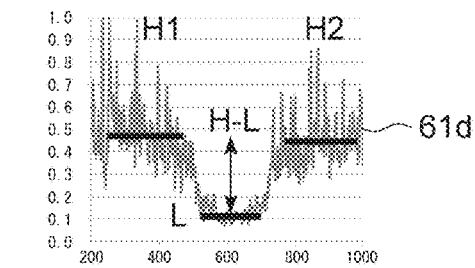
Figure 10C:
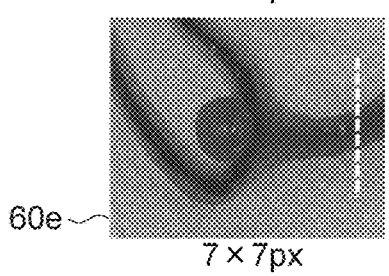
Figure 10C:
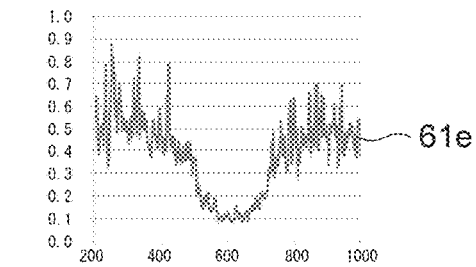
Figure 10D:
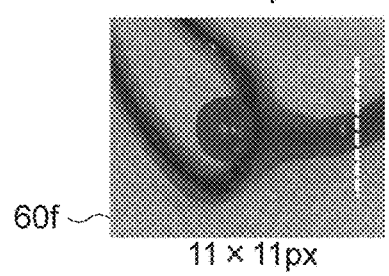
Figure 10D:
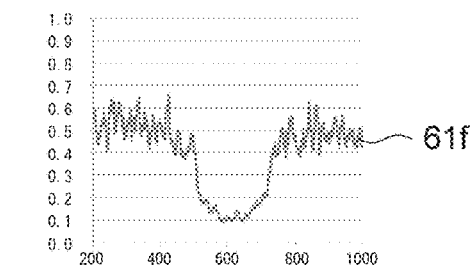
Figure 10E:
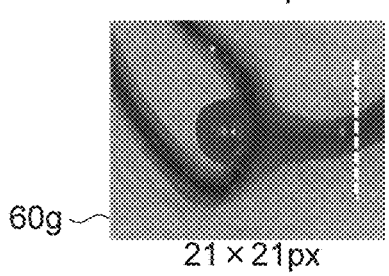
Figure 10E:
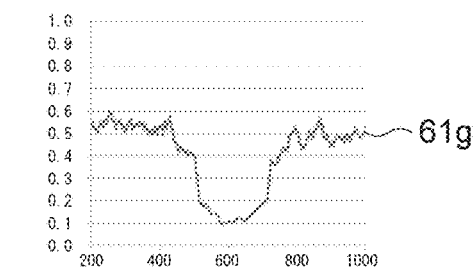
Figure 10F:
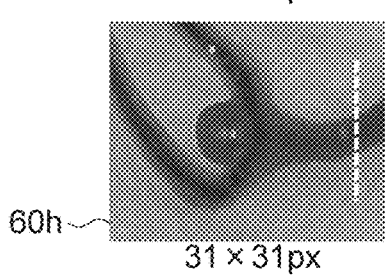
Figure 10F:
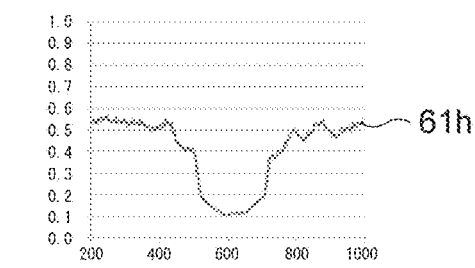

FIGS. 9A, 9B, and 9C is a are schematic diagrams for explaining a relationship between a cell size and a speckle contrast. In FIGS. 9A, 9B, and 9C, speckle contrasts Cs for respective cells 42*c* to 42*e* are calculated respectively using first to third cell sizes that are different from one another. Note that, in FIGS. 9A, 9B, and 9C, a speckle image 50*d* is used in common. For example, the speckle image 50*d* is an image of the high contrast portion 52 described in FIGS. 7A and 7B.

FIG. 9A schematically illustrates the speckle image 50*d* divided in a first cell size (on the left), a luminance distribution of respective cells 42*c* (in the central portion), and a speckle contrast Cs calculated for each cell 42*c* (on the right).

The first cell size is a size similar to a speckle size (speckle particle size) of the speckle image 50*d*. As shown on the left in FIG. 9A, examples of the cells 42*c* obtained by dividing the speckle image 50*d* include, for example, a cell 42*c* surrounding one speckle, a cell 42*c* partially including a speckle, and a cell 42 not including a speckle. For example, regarding a cell 42*c* situated at a coordinate (4,1), the cell 42*c* is substantially occupied by one speckle. Further, for example, a cell 42*c* situated at, for example, a coordinate (0,2) does not include a speckle.

As shown in the graph situated in the central portion of FIG. 9A, a luminance distribution of the respective cells 42c obtained by the division performed in the first cell size is a distribution depending on, for example, a proportion of a speckle included in each cell 42c. For example, a cell 42c occupied by a speckle exhibits a high average luminance and thus its luminance distribution has a small width, and a cell not including a speckle exhibits a low average luminance and thus its luminance distribution has a small width. Further, for example, a cell 42c partially including a speckle exhibits a luminance distribution having a large width.

On the right in FIG. 9A, each cell 42c obtained by the division performed in the first cell size is shown at a brightness depending on the speckle contrast Cs of the cell 42c. Each cell 42c forms a random light and dark pattern depending on a speckle pattern of the speckle image 50d. Further, the proportion of a cell 42c of a black color, that is, the proportion of a cell 42c exhibiting a luminance distribution of a small width is high, and this results in an overall dark screen.

FIG. 9B, a second cell size that is larger than the first cell size is used. The second cell size is about four times as large as the first cell size. As shown in the graph situated in the central portion of FIG. 9B, respective cells 42d obtained by dividing the speckle image 50d in the second cell size each exhibit a luminance distribution having a larger width in totality, compared to using the first cell size. Consequently, values of speckle contrasts Cs of the respective cells 42d become large in totality. For example, as shown on the right in FIG. 9B, when the second cell size is used, the proportion of a cell 42d being brightly displayed is increased.

FIG. 9C, a third cell size that is larger than the second cell size is used. As shown on the left in FIG. 9C, all of the cells 42e obtained by dividing the speckle image 50d in the third cell size each include a speckle and a surrounding region around the speckle. Thus, the respective cells 42e exhibit the same luminance distribution having a large width. Thus, as shown on the right in FIG. 9C, the speckle contrasts Cs of the respective cells 42d obtained by the division performed in the third cell size have values that are substantially equal to one another and are large (high-luminance values).

As described above, the speckle contrast Cs of a cell 42c, 42d, 42e has a value depending on the proportion of the area of a speckle included in the cell 42c, 42d, 42e. In other words, the value of a speckle contrast Cs is determined depending on the ratio between a speckle size and a cell size in the speckle image 50d. This makes it possible to calculate a speckle contrast Cs exhibiting a small variation and having a large value by, for example, making a cell size large.

FIGS. 10A, 10B, 10C, 10D, 10E, and 10F are diagrams for explaining a relationship between a cell size and a speckle contrast image. FIGS. 10A 10B 10C, 10D, 10E, and 10F respectively illustrate speckle contrast images 60c to 60h respectively calculated in cell sizes of 3×3, 5×5, 7×7, 11×11, 21×21, and 31×31. Raw images (speckle images) in FIGS. 10A, 10B, 10C, 10D, 10E, and 10F are obtained by performing image-capturing on the blood vessel phantom 70 described in, for example, FIG. 5. Note that the blood vessel clip 73 or the like is not used in the raw images in FIGS. 10A, 10B, 10C, 10D, 10E, and 10F.

Further, FIGS. 10A, 10B, 10C, 10D, 10E, and 10F respectively illustrate line profiles 61c to 61h of speckle contrasts Cs in the respective speckle contrast images 60c to 60h. The line profiles 61c to 61h are line profiles each being along a straight line 45 that intersects the blood vessel 71 shown on the right. In each of the line profiles 61c to 61h, a central portion exhibiting a small value corresponds to a region of the blood vessel 71, and two portions being situated on both sides of the central portion and exhibiting a large value, correspond to a region of a background 77. Note that, in FIGS. 10A, 10B, 10C, 10D, 10E, and 10F, the speckle contrast Cs is normalized such that the maximum value is 1.

For example, when the 3×3 cell size is used, the value of a speckle contrast Cs calculated for each pixel exhibits a great variation (noise), as shown by the line profile 61c. Thus, in a speckle contrast image 60c generated in the 3×3 cell size, a fine light and dark spot pattern (glare) is produced.

When the 5×5 cell size is used, the width of a variation in the value of a speckle contrast in the line profile 61d is smaller than that of the variation in the case of the 3×3 cell size. Note that, in the line profile 61d of the 5×5 cell size, a region L corresponding to the blood vessel 71 and regions H1 and H2 corresponding to the background 77 situated on both sides of the blood vessel 71 are schematically illustrated using black lines.

The variation in the value of a speckle contrast Cs calculated for each pixel is decreased with an increase in a cell size. For example, in the speckle contrast image 60g generated in the 21×21 cell size, glare due to a spot pattern is nearly invisible.

Note that the resolution of a speckle contrast image is reduced with an increase in a cell size. For example, in the region corresponding to the blood vessel 71 in the line profile 61h of the 31×31 cell size, a fine structure is invisible that is visible in, for example, the line profile 61e of the 7×7 cell size and the line profile 61f of the 11×11 cell size. Thus, in the speckle contrast image 60h generated in the 31×31 cell size, it is difficult to recognize, for example, a distribution of fine lightness and darkness in the blood vessel 71.

Figure 11A:
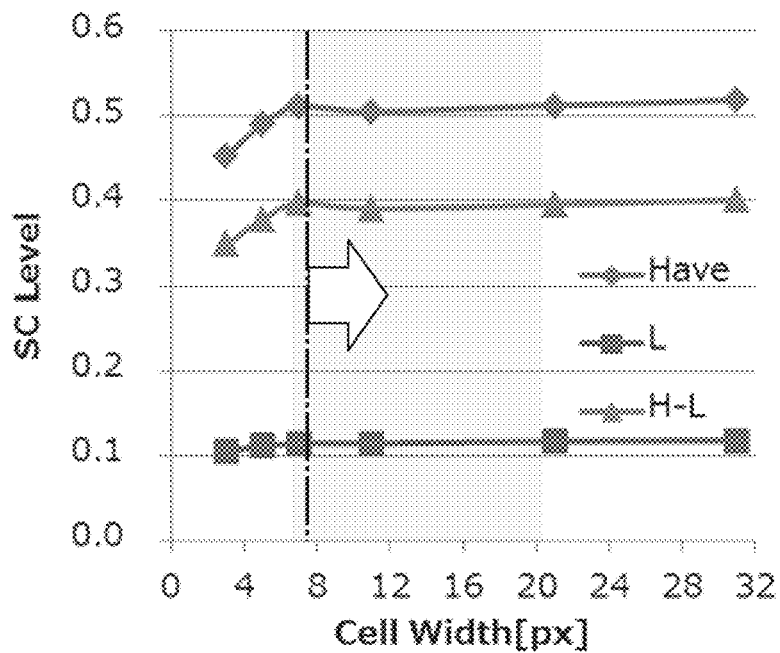
FIGS. 11A and 11B is a are diagrams for explaining the characteristics of a speckle contrast.
Figure 11B:
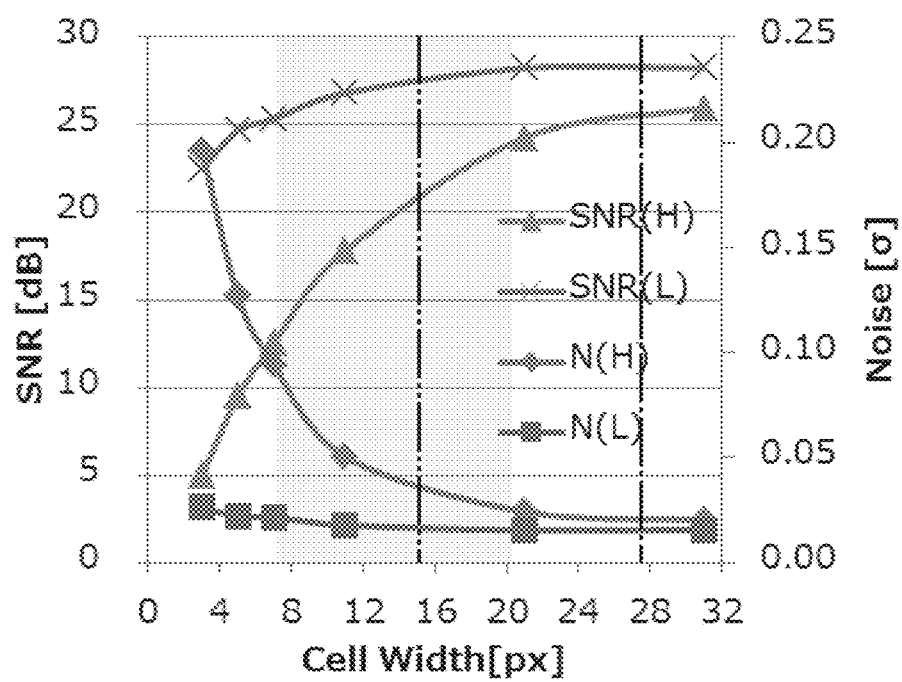

FIGS. 11A and 11B are diagrams for explaining the characteristics of a speckle contrast. FIG. 11A is a graph illustrating a relationship between a cell size and a speckle contrast Cs in each of the line profiles 61c to 61h illustrated in FIGS. 10A 10B, 10C, 10D, 10E, and 10F. A square data point represents an average of a speckle contrast Cs in the region L corresponding to the blood vessel 71. A rhombic data point represents an average of a speckle contrast Cs in the regions H1 and H2 corresponding to the background 77. A triangular data point represents a difference between the average of a speckle contrast Cs in the blood vessel 71, and the average of a speckle contrast Cs in the background 77.

The average of a speckle contrast Cs in the blood vessel 71 does not vary greatly with an increase in a cell size. On the other hand, the average of a speckle contrast Cs in the background 77 increases greatly in the case of the 3×3 cell size to the 7×7 cell size, and increases gradually in the case of the cell sizes of 7×7 or more. Thus, for example, the difference in brightness between the blood vessel 71 through which blood is flowing, and the background 77 (the triangular data point) does not vary greatly even in the case of the cell size of 7×7 or more.

FIG. 11B is a graph illustrating a relationship between a cell size, and noise N and a signal-noise ratio SNR of a speckle contrast Cs in each of the line profiles 61c to 61h illustrated in FIGS. 10A, 10B, 10C, 10D, 10E, and 10F. In the graph, the vertical axis on the left corresponds to a signal-noise ratio of a speckle contrast Cs, and the horizontal axis on the right corresponds to noise of the speckle contrast Cs.

For example, noise N(L) (the square data point) of the speckle contrast Cs of the blood vessel 71 is reduced when the cell size is from 3×3 to about 15×15, and in the case of a larger cell size, the noise N(L) is hardly changed. The signal-noise ratio SNR(L) (X-mark data point) of the blood vessel 71 is increased by about 10 dB if the noise N(L) is reduced.

Further, noise N(H) (the rhombic data point) of a speckle contrast Cs of the background 77 is reduced when the cell size is from 3×3 to about 30×30, and in the case of a larger cell size, the noise N(L) is hardly changed. Moreover, when the ratio between the speckle contrast Cs and the noise of the background 77 is SNR(H) (the rectangular data point), SNR(H) is increased by about 20 dB if the noise N(L) is reduced.

As described above, in a speckle contrast image, for example, glare, brightness, and resolutions of the blood vessel 71 and the background 77 vary depending on a cell size, and how the speckle contrast image looks is changed. Thus, the change in a cell size makes it possible to change the image quality of an observation image (a speckle contrast image) to perform observation. For example, when there is a need to observe the observation target site 2 in detail, it is possible to generate a high-resolution observation image by making the cell size small. Further, for example, when there is a need to roughly grasp a site with blood flow (the blood vessel 71), it is also possible to make the cell size large and to uniformly display a region with blood flow and a region without blood flow at respective brightnesses. However, it is not possible to make the cell size larger than the width of an observation target blood vessel, so there is a limitation.

Figure 12A:
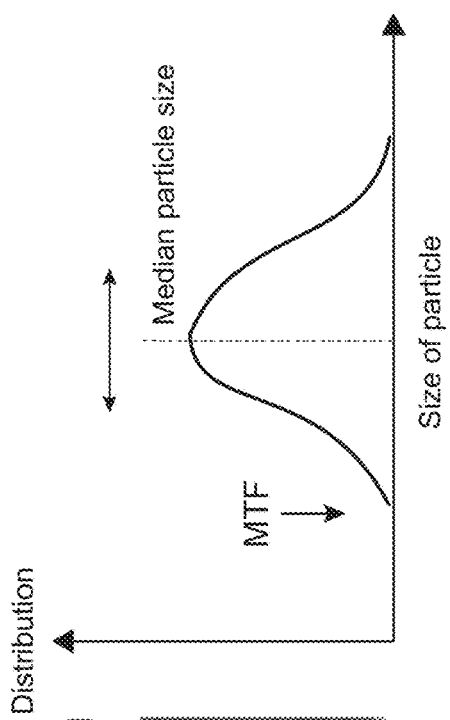
FIGS. 12A and 12B is a are diagrams for explaining about a speckle size in a speckle image.
Figure 12A:
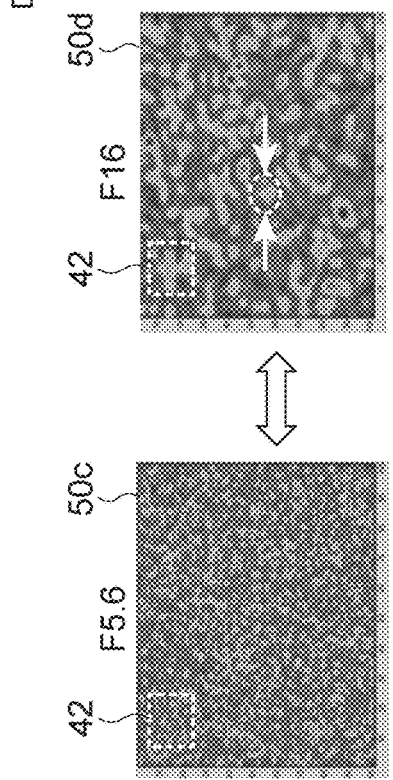
Figure 12B:
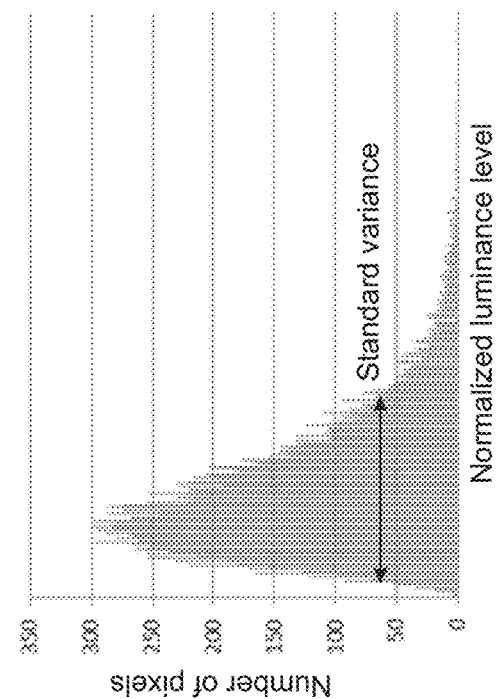

FIGS. 12A and 12B are diagrams for explaining about a speckle size in a speckle image. FIG. 12A illustrates a speckle image 50c (on the left) captured with the f-number of the lens section 21 being 5.6, and a speckle image 50d (on the right) captured with the f-number of 16. FIG. 12B is a graph of a luminance distribution in the cell 42 in the speckle image 50c captured with the f-number of 5.6.

When the f-number of the lens section 21 is 5.6, the speckle image 50c having, on an entire screen, a spot pattern of a small particle size, is captured. This spot pattern corresponds to a speckle. In the speckle image 50d captured with the f-number of the lens section 21 being 16, the sizes of respective spots (speckle sizes) are larger in totality, compared to when the f-number is 5.6. Note that, in the speckle image 50d, a spot corresponding to one speckle is schematically illustrated using a dotted line.

FIG. 12A includes, on the right, a schematic graph of a distribution of the particle size of a speckle (speckle size) included in the speckle image 50. The distribution of the particle size of a speckle is an arched distribution having a median particle size at its peak. Note that the minimum value of the particle size of a speckle is represented using, for example, a modulation transfer function (MTF) of, for example, the lens section 21.

The median particle size of a speckle in the speckle image 50 varies with a change in an imaging parameter such as the f-number of the lens section 21. For example, when the f-number is changed from 5.6 to 16, the size of a speckle appearing in the speckle image 50 is large in totality. Consequently, the median particle size of a speckle is increased, and the entire distribution of a speckle particle size is shifted to the right. As described above, the size of a speckle included in the speckle image 50 varies depending on, for example, an imaging parameter.

Note that, as described in, for example, FIGS. 9A, 9B, and 9C, the speckle contrast Cs is calculated using a luminance distribution in a cell 42 depending on a cell size and a size of a speckle. For example, when the same cell size is used, a luminance distribution in a cell 42 of the speckle image 50c captured with the f-number of 5.6 (refer to FIG. 12B), and a luminance distribution in a cell 42 of the speckle image 50d captured with the f-number of 16 are different. Thus, different speckle contracts Cs are respectively calculated for the speckle images 50c and 50d.

FIGS. 13A and 13B is a are diagrams illustrating a relationship between a speckle size and an imaging parameter at 1× optical magnification with a wavelength of 850 nm and a pixel size of 5.8 microns. FIG. 13A illustrates speckle images 50e, 50c, and 50d respectively captured with the f-numbers of 2, 5.6, and 16. As illustrated in FIG. 13A, the size of a speckle appearing in each speckle image 50 becomes larger as the f-number is increased.

FIG. 13B is a graph illustrating a relationship between a speckle size and an f-number. The horizontal axis of the graph represents an f-number at the time of capturing the speckle image 50. Further, the vertical axis represents a full width of a speckle (the size of a speckle) in the speckle image 50 captured with each f-number. Here, the full width of a speckle is, for example, the median particle size of a speckle described using the graph in FIG. 13A.

The graph illustrated in FIG. 13B shows both an experimental value (rhombic data point) and a calculation value (square data point) of the full width of a speckle. The experimental value of the full width of a speckle is calculated by, for example, obtaining cross-correlation between an image obtained by shifting the speckle image 50 and the speckle image 50 before the shifting. Further, the calculation value of the full width of a speckle is calculated using, for example, simulation. The method for calculating an experimental value and a calculation value of the full width of a speckle or the like is not limited, and an arbitrary method that makes it possible to calculate, for example, the particle size of a speckle, may be used as appropriate.

As illustrated in FIG. 13B, when the f-number is not greater than four (for example, F #=1.4, 2, or 2.8), the experimental value and the calculation value of the full width of a speckle are both about one pixel. In this case, the speckle appearing in the speckle image 50 is smaller than one pixel.

B of FIG. 13 is a graph illustrating a relationship between a speckle size and an f-number. The horizontal axis of the graph represents an f-number at the time of capturing the speckle image 50. Further, the vertical axis represents a full width of a speckle (the size of a speckle) in the speckle image 50 captured with each f-number. Here, the full width of a speckle is, for example, the median particle size of a speckle described using the graph in A of FIG. 13.

The graph illustrated in B of FIG. 13B shows both an experimental value (rhombic data point) and a calculation value (square data point) of the full width of a speckle. The experimental value of the full width of a speckle is calculated by, for example, obtaining cross-correlation between an image obtained by shifting the speckle image 50 and the speckle image 50 before the shifting. Further, the calculation value of the full width of a speckle is calculated using, for example, simulation. The method for calculating an experimental value and a calculation value of the full width of a speckle or the like is not limited, and an arbitrary method that makes it possible to calculate, for example, the particle size of a speckle, may be used as appropriate.

As illustrated in B of FIG. 13, when the f-number is not greater than four (for example, F #=1.4, 2, or 2.8), the experimental value and the calculation value of the full width of a speckle are both about one pixel. In this case, the speckle appearing in the speckle image 50 is smaller than one pixel.

When the f-number is greater than four, the experimental value and the calculation value of the full width of a speckle are both increased with an increase in the f-number. The amount of an increase in the width of a speckle is nearly linear with respect to the amount of an increase in the f-number. Note that there is a possibility that a change in an imaging parameter other than an f-number will also result in a change in the width of a speckle. For example, when the optical magnification of the lens section 21 is increased, the width of a speckle is also increased nearly linearly.

Further, as illustrated in FIG. 13B, the experimental value and the calculation value of the full width of a speckle match with a high degree of precision. Thus, for example, it is possible to accurately calculate, for example, the size (the full width) of a speckle in a captured speckle image 50 from an f-number used to capture the image. Of course, the imaging parameter used to calculate the size of a speckle is not limited to an f-number, and other parameters such as an optical magnification may be used.

As described above, when an imaging parameter such as an f-number is changed, the size of a speckle appearing in a speckle image 50 has a value depending on the imaging parameter. Thus, with an increase in an imaging parameter (a change in the size of a speckle), the value of a speckle contrast Cs calculated from the speckle image 50 is also changed, and the image quality of a speckle contrast image 60 (an observation image) is changed.

Figures 14, 15:
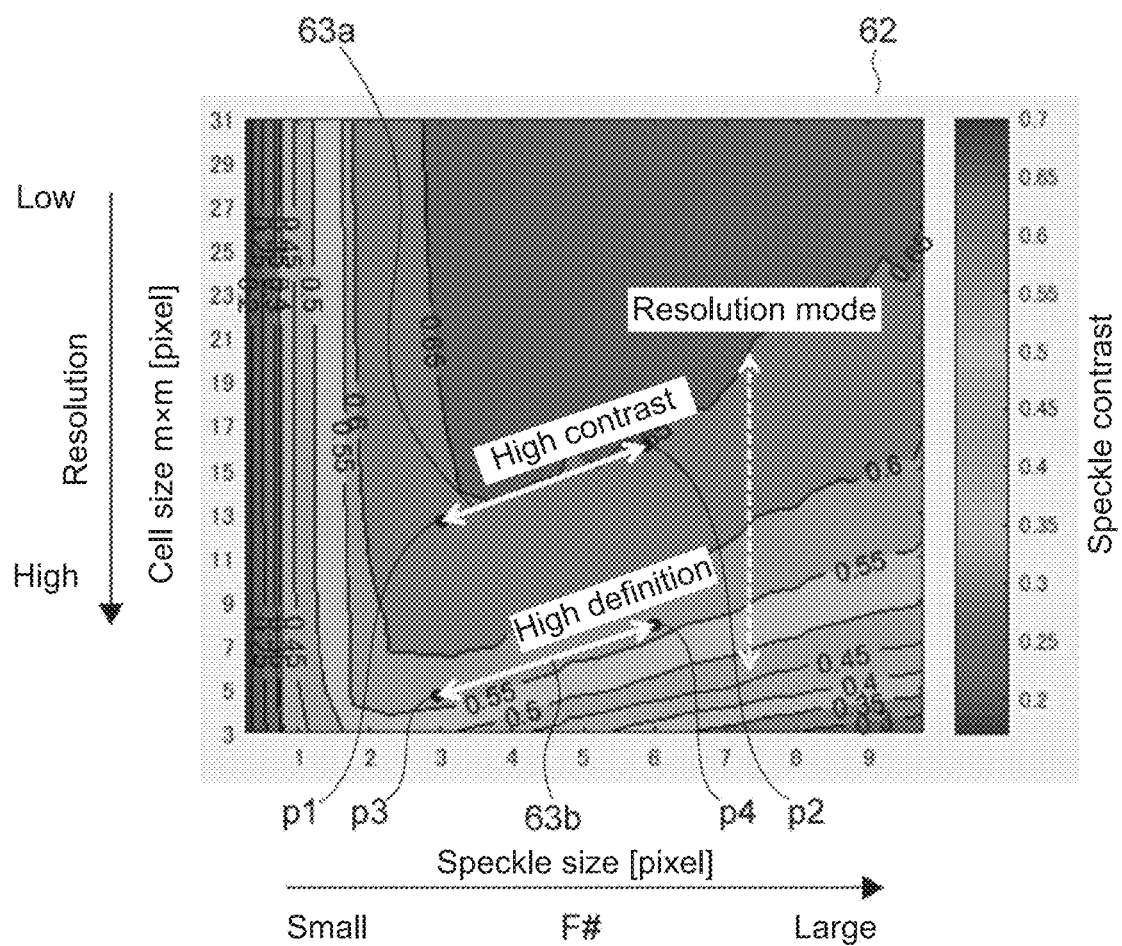
FIG. 14 illustrates an example of a map of a speckle contrast regarding a speckle size and a cell size.
FIG. 15 is a diagram illustrating an example of a processing size table.

FIG. 14 illustrates an example of a map 62 of a speckle contrast regarding a speckle size and a cell size. The horizontal axis of the map 62 represents a speckle size, and the vertical axis represents a cell size. Note that, in FIG. 14, a square cell 42 in which the number of pixels in a longitudinal direction and the number of pixels in a lateral direction are equal to each other, is used, and the cell size corresponds to the number of pixels in the longitudinal (lateral) direction.

The map 62 illustrated in FIG. 14 shows a value of a speckle contrast Cs using isopleths on a 0.05 basis. The value of the speckle contrast Cs in the map 62 is calculated by, for example, simulating the value of a speckle contrast Cs in each speckle size d and in each cell size s. The map 62 illustrated in FIG. 14 will be hereinafter referred to as a contrast map 62. Further, the position of each point in the contrast map 62 will be referred to as (d,s), using the speckle size d and the cell size s.

Note that the method for generating the contrast map 62 or the like is not limited, and the speckle contrast Cs may be calculated using, for example, an actually captured speckle image 50 of a sample of, for example, a standard diffuser. In this case, it is possible to generate the contrast map 62 by, for example, changing the cell size for each speckle size S (imaging parameter) and calculating a speckle contrast. Moreover, an arbitrary method that makes it possible to generate the contrast map 62.

As illustrated in FIG. 14, in the contrast map 62, it is possible to select a combination of a speckle size S and a cell size C such that the value of a speckle contrast Cs is substantially constant. For example, the value of a speckle contrast Cs is substantially constant (about 0.65) at each point on a linear first route 63a (an arrow 63a in the figure) that connects a point p1 (3,13) and a point p2 (6,16).

For example, it is assumed that a speckle contrast image 60 is generated under the same condition as that for each point on the first route 63a, that is, the speckle contrast image 60 is generated using a speckle size and a cell size that correspond to each point on the first route 63a. In this case, the value of a speckle contrast Cs on the first route 63a is constant (about 0.65), so the light and dark contrasts of speckle contrast images 60 generated under the respective conditions are substantially identical to one another. In the present embodiment, the light and dark contrast of a speckle contrast image 60 corresponds to a specified display parameter related to a display luminance of an observation image.

As described above, it is possible to keep the light and dark contrast (display parameter) of a speckle contrast image 60 substantially constant by selecting a cell size C according to the first route 63a when the speckle contrast image 60 is generated. Consequently, for example, even if there is a change in a speckle size by an imaging parameter being changed due to, for example, a zoom function, a speckle contrast image 60 of the same contrast will be acquired by setting a cell size according to the change.

Likewise, the value of a speckle contrast Cs is also kept substantially constant (about 0.56) on a second route 63b (an arrow 63b in the figure) that connects a point p3 (3,5) and a point p4 (6,8). Thus, the light and dark contrast of a speckle contrast image 60 generated under the same condition as that for each point on the second route 63b has a substantially constant value corresponding to the value of a speckle contrast Cs (about 0.56) on the second route 63b.

Note that, in a contrast map 62, the route that keeps the value of a speckle contrast substantially constant is not limited to the first and second routes 63a and 63b. For example, it is also possible to generate a speckle contrast image 60 along a route other than the first and second routes 63a and 63b that is situated between the first and second routes 63a and 63b.

As described above, it is possible to control the image quality of a speckle contrast image 60 (observation image) by generating the speckle contrast image 60 along a route that keeps the value of a speckle contrast Cs in a contrast map 62 substantially constant. For example, it is possible to generate observation images in a plurality of image quality modes whose respective image qualities are different from one another, by controlling the cell size along the respective routes.

In image quality modes corresponding to respective routes, the value of a speckle contrast Cs is kept substantially constant in respective ranges of a cell size that are different from one another. Thus, it is possible to select the range of a display resolution of an observation image by selecting the image quality mode corresponding to each route. For example, the range of a display resolution (cell size s) of an image quality mode corresponding to the second route 63b, is from 5 to 8 pixels. In the present embodiment, the image quality mode corresponding to each route corresponds to an image quality mode related to a display resolution.

For example, the cell-size range corresponding to the second route 63b is a range whose cell size has a smaller value than that of the first route 63a. Thus, the speckle contrast image 60 generated along the second route 63b is a high-definition image whose display resolution is higher than that of a speckle contrast image 60 generated along the first route 63a. In the present embodiment, the image quality mode corresponding to the second route 63b corresponds to a second image quality mode in which priority is given to a display resolution.

Further, for example, the first route 63a is a route whose speckle contrast Cs has a value larger than that of the second route 63b. Thus, in the speckle contrast image 60 generated along the first route 63a, a speckle contrast Cs is calculated that is overall higher than that of a speckle contrast image 60 generated along the second route 63b, and a sharp image of a high light and dark contrast is acquired. In other words, in the present embodiment, an image quality mode corresponding to the first route 63a corresponds to a first image quality mode in which priority is given to contrast display over a resolution.

Note that a large cell size C is used for an image quality mode corresponding to the first route 63a. Thus, in a speckle contrast image 60 generated along the first route 63a, respective portions, such as the blood vessel 71 and the aneurysm 72, of the observation target site 2 are substantially uniformly displayed at respective brightnesses (refer to FIG. 8). Thus, the selection of an image quality mode corresponding to the first route 63a makes it possible to generate a high contrast image in which, for example, the difference in display luminance between the low contrast portion 51 (the blood vessel 71) and the high contrast portion 52 (aneurysm 72) is clear.

FIG. 15 is a diagram illustrating an example of the processing size table 38. The processing size table 38 is generated using the contrast map 62, and stored in the storage 37. A cell size (a processing size) corresponding to a speckle size is recorded in the processing size table 38 for each image quality mode A to E.

In the example illustrated in FIG. 15, the image quality mode is classified into five stages that are the image quality modes A to E. Further, the range of a speckle size is classified into four stages that are 3 to 6 pixels. The methods for classifying an image quality mode and a speckle size are not limited, and may be set discretionally.

For example, the image quality mode B is an image quality mode corresponding to a route in which the value of a speckle contrast Cs in a contrast map 62 is about 0.6. In other words, the image quality mode B is a mode in which a cell size is controlled with respect to each speckle size, such that a speckle contrast in a contrast map 62 is about 0.6. Note that the image quality mode A corresponds to an image quality mode corresponding to the second route 63b illustrated in FIG. 14, and the image quality mode E corresponds to an image quality mode corresponding to the first route 63a.

Figure 16:
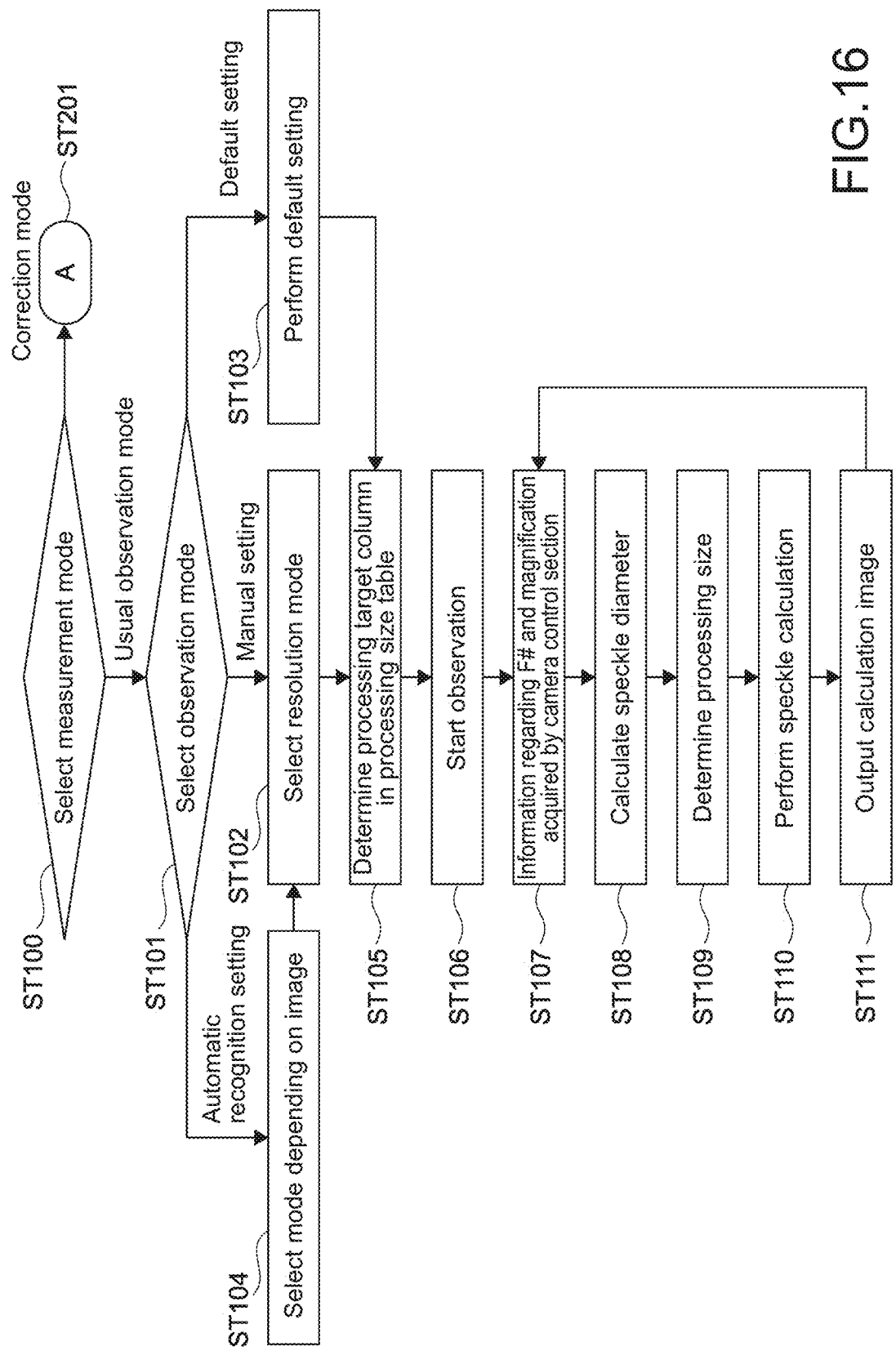
FIG. 16 is a flowchart of an example of a basic operation of the observation system.

FIG. 16 is a flowchart of an example of a basic operation of the observation system 100. First, a measurement mode in the observation system 100 is selected by an operator who operates the observation system 100 through, for example, an operation screen. The selected measurement mode is received by the UI acquisition section 34 (Step 100).

The measurement mode includes a usual observation mode in which usual observation is performed, and a correction mode in which the observation system 100 is corrected. When the selection of a usual observation mode is received, Step 101 is performed. Further, when the selection of a correction mode is received, Step 201 is performed to start a correction mode. The correction mode will be described in detail later.

When the usual observation mode is selected, a selection screen used to select an observation mode is displayed on the operation screen. The observation mode includes a manual setting mode, a default setting mode, and an automatic recognition mode. An observation mode is selected by the operator, and the selected observation mode is received by the UI acquisition section 34 (Step 101).

When the manual setting mode is selected, a selection screen used to select a resolution mode is displayed on the operation screen. The resolution mode includes the image quality modes A to E in the processing size table 38 illustrated in FIG. 15. One of the image quality modes A to E displayed on the selection screen is selected by the operator. The selected image quality mode is received by the UI acquisition section 34 as a resolution mode (Step 102).

For example, when there is a need to generate an observation image with a high-resolution and high-definition image quality, the image quality mode A is selected. Further, for example, when there is a need to distinguish the blood vessel 71 and a region other than the blood vessel 71 from each other by use of the difference in brightness, that is, when there is a need to observe the blood vessel 71 and a region other than the blood vessel 71 with a high contrast, the image quality mode E is selected. Of course, the selection of an image quality mode is not limited to this, and an image quality mode desired by an operator may be selected as appropriate. Note that the image quality modes A to E may be respectively displayed on a selection screen using picture images such as icons that respectively represent the characteristics of the respective modes. This makes it possible to select an image quality mode intuitively.

When the default setting mode is selected, an image quality mode set by default for the observation system, is set to be a resolution mode (Step 103). For example, from among the image quality modes A to E, an image quality mode C having a display resolution of a substantially medium range, is set to be the default image quality mode. Of course, one of the other image quality modes may be set to be a default. When the resolution mode is set to a default value, Step 105 is performed.

When the automatic recognition mode is selected, an image quality mode is selected using an image of the observation target site 2 (Step 104). For example, the image quality mode is selected depending on the size of the blood vessel 71 in an image-capturing range of the observation target site 2. The selected image quality mode is set to be a resolution mode in Step 102. Note that the size of the blood vessel 71 is identified using an image of the observation target site 2 that is captured using a reagent such as indocyanine green (ICG).

In Step 104, it is determined, from the image of the observation target site 2 captured using, for example, ICG, whether the blood vessel 71 included in the observation target site 2 is a large blood vessel 71 such as a cerebral aneurysm or a small blood vessel 71 such as a perforating branch. The method for determining, for example, the size of the blood vessel 71 from an image of the observation target site 2 is not limited, and an arbitrary method using, for example, machine learning or image processing may be used.

For example, with respect to the large blood vessel 71 including a cerebral aneurysm, an image quality mode in which priority is given to a display luminance or the like, is selected in order to clearly distinguish between the blood vessel 71 and the cerebral aneurysm. Further, when importance is placed on the observation of blood flow in the small blood vessel 71, an image quality mode with a high resolution is selected. Moreover, an appropriate image quality mode may be selected as appropriate depending on an image of the observation target site 2 according to, for example, a state of the blood vessel 71 or the type of a tissue of a living body. Note that the image used to identify, for example, the size of the blood vessel 71 is not limited to an image captured using, for example, ICG, and an image of the observation target site 2 that is captured by any other method or the like may be used as appropriate.

Note that the selections of a measurement mode, an observation mode, and a resolution mode in Step 100, 101, and 102 may be performed at arbitrary timings. In other words, the UI acquisition section 34 is capable of constantly receiving, for example, a selection performed by an operator. In this case, the processes starting from Step 100, 101, and 102 are respectively restarted at timings at which the respective modes are selected.

A processing target column in the processing size table 38 is determined according to the resolution mode set in Step 102 (Step 105). For example, when the image quality mode A is set to be the resolution mode, the processing target column is the first column. Information regarding the determined processing target column is output to the processing-size control section 41 (the block control section 35).

An image of the observation target site 2 onto which laser light is irradiated is captured by the camera 20 that captures an image of the observation target site 2 (Step 106). An image signal of the image of the observation target site 2 captured by the camera 20, is generated, and acquired by the image acquisition section 32. Imaging parameters such as an f-number F # and an optical magnification M of the camera 20 are acquired by the camera control section 33 (Step 107). The acquired imaging parameters are output to the predicted-speckle-size calculator 40.

A speckle size is calculated by the predicted-speckle-size calculator 40 using the imaging parameters (Step 108). The speckle size is calculated using the speckle size calculating formula described above. Note that the speckle size calculated in Step 108 corresponds to a particle size in a speckle in a speckle image 50 formed by the image signal of the image captured in Step 106. The calculated speckle size is output to the processing-size control section 41.

A cell size is determined by the processing-size control section 41 (Step 109). The processing-size control section 41 determines a cell size from the processing size table 38, according to the processing target column (image quality mode) determined in Step 105, and according to the speckle size calculated in Step 108. The determined cell size is output to the speckle calculation section 36.

A speckle contrast is calculated by the speckle calculation section 36 using the image signal of the observation target site 2 that is acquired by the image acquisition section (Step 110). The speckle contrast Cs is calculated using the cell size determined by the processing-size control section 41.

The speckle calculation section 36 generates a speckle contrast image 60 that is an observation image of the observation target site 2, according to the calculated speckle contrast Cs (Step 111). As described above, the use of a cell size controlled by the processing-size control section 41 makes it possible to generate an observation image with an image quality corresponding to a set resolution mode. The generated observation image is output to a display. This enables an operator to observe an observation image of the observation target site 2 with a desired image quality.

As illustrated in FIG. 16, in the observation system 100, a loop process of respective steps from Step 107 to Step 111 is performed. In other words, an imaging parameter is acquired for each loop process, and according to the acquired imaging parameter, an observation image is generated with an image quality corresponding to a set resolution mode.

For example, when an operator magnifies the observation target site 2 using, for example, a zoom function of the lens section 21 to capture an image of the observation target site 2, the image parameters such as an optical magnification M and an f-number F # are changed, and a speckle size in a speckle image 50 is changed. The processing-size control section 41 determines a cell size depending on the speckle size in a range of a display resolution (a range of the cell size) in a resolution mode. In other words, the cell size is controlled by the processing-size control section 41 such that the display parameters regarding a display luminance of an observation image are kept substantially constant in a range of a display resolution with respect to a plurality of image quality modes.

Note that the loop process including Step 107 to Step 111 is stopped, for example, at a timing at which a resolution mode or the like is updated. For example, when another image quality mode is selected by an operator, the loop process is stopped and Step 102 is performed. This enables the operator to change the image quality of an observation image at his/her desired timing.

Figure 17:
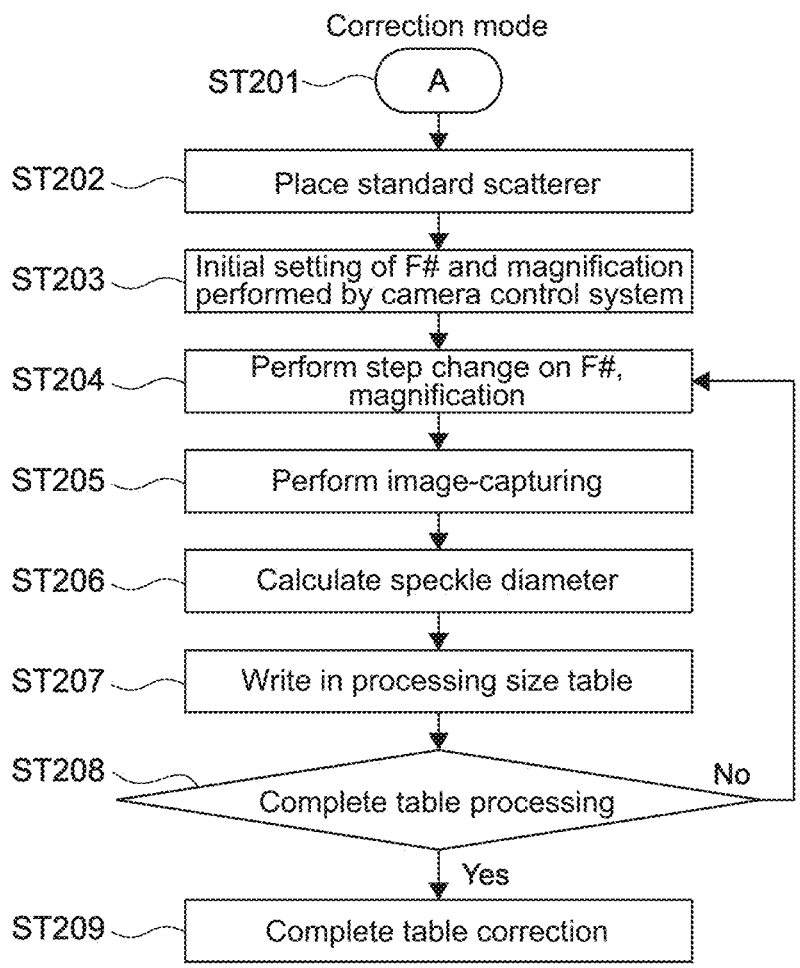
FIG. 17 is a flowchart of an example of correcting the observation system.

FIG. 17 is a flowchart of an example of correcting the observation system 100. The observation system 100 is corrected, for example, at a timing of a replacement of the lens section 21 or the like. The timing of correcting the observation system 100 is not limited, and the observation system 100 may be corrected at any timing.

In the present embodiment, a correction of the processing size table 38 is performed as the correction of the observation system 100. In other words, it can also be said that the processing size table 38 is newly generated at a timing of a replacement of the lens section 21 or the like, in which the characteristics of the lens section 21 after the replacement is reflected in the newly generated processing size table 38. The processing size table 38 is corrected using a standard scatterer. For example, a reflective standard scatterer in which particles of a uniform particle size adhere to the surface of the reflective standard scatterer or the like, is used as the standard scatterer. The type of standard scatterer or the like is not limited, and any scatterer may be used. In the present embodiment, the standard scatterer corresponds to a specified target for correction.

When the correction mode is selected as a measurement mode in Step 100 illustrated in the flowchart of FIG. 16, Step 201 is performed to start performing processing in the correction mode. First, a standard scatterer is placed in an image-capturing range of the camera 20 (Step 202). The standard scatterer is arranged, for example, at the same position as the observation target site 2, and is irradiated with the laser light 11. The position at which a standard scatterer is arranged or the like is not limited, and, for example, the standard scatterer may be arranged at an arbitrary position at which the standard scatterer can be irradiated with laser light 11 and an image of the standard scatterer can be captured.

Image parameters such as an f-number F # and an optical magnification M of the camera 20 are set to specified values such as initial setting values by the camera control section 33 (Step 204). The values to which the imaging parameters are set, are not limited, and, for example, they may be set to, for example, the minimum values of the f-number F # and the optical magnification M or the like.

At least one of the f-number F # or the optical magnification M is changed by the camera control section 33, the f-number F # and the optical magnification M being respectively changed by respective step amounts (Step 204). In Step 204, a different combination of an f-number F # and an optical magnification M is set by the camera control section 33 every time the loop process in the flowchart is performed. In other words, in Step 204, each imaging parameter is set such that an f-number F # and an optical magnification M are combined in a round robin manner with respect to respective executions of the loop process. The order of setting the respective combinations or the like is not limited. Note that the specified values set in Step 203 are used when the process is performed for the first time.

An image of the standard scatterer irradiated with the laser light 11 is captured by the camera 20 (Step 205). An image signal of the captured image is acquired by the image acquisition section 32 and output to an image processing section. The image processing section is capable of performing any image processing on a speckle image formed by, for example, the image signal. Note that an illustration of the image processing section is omitted in FIG. 1. A speckle size (speckle particle size) in a speckle image is calculated by the image processing section using the speckle image of the standard scatterer (Step 206).

The processing size table 38 is corrected according to the calculated speckle size (Step 207). For example, a cell size corresponding to the speckle size calculated in Step 206 is acquired for each pixel mode according to the contrast map 62 illustrated in FIG. 14, and is recorded in the processing size table 38.

It is determined whether data necessary for the processing size table 38 is ready (Step 208). For example, it is determined whether the number of speckle sizes necessary in the processing size table 38 is ready. For example, four speckle sizes are recorded in the processing size table illustrated in FIG. 15. The number of speckle sizes used for the processing size table 38 is not limited, and, for example, it may be set as appropriate depending on, for example, the accuracy in the processing size table 38 or the characteristics of the lens section 21.

When it is determined that data necessary for the processing size table 38 is not ready (No in Step 208), Step 204 is performed again. In other words, the imaging parameter of the camera 20 is changed and the process of calculating a speckle size is performed again. Further, when it is determined that data necessary for the processing size table 38 is ready (Yes in Step 208), the process performed on the processing size table 38 in the correction mode is terminated (Step 209).

As described above, a speckle size depending on the f-number F # and the optical magnification M set in Step 206, and a cell size corresponding to the speckle size for each pixel mode are recorded in the processing size table 38. Thus, the values in the processing size table 38 are corrected to values suitable for the lens section 21 after replacement.

For example, the maximum value or the minimum value of a speckle size of which an image is captured or the like, may vary by, for example, a replacement of the lens section 21. In this case, it is difficult to calculate a speckle size with a high degree of accuracy using the processing size table 38 used before the replacement of the lens section 21. The correction of the processing size table 38 according to the lens section 21 makes it possible to perform a process that can sufficiently cope with a change in an imaging parameter (speckle size).

Note that, in the flowchart illustrated in FIG. 17, the speckle size is measured from the actually measured speckle image 50. The speckle size calculating formula used to calculate a speckle size using an imaging parameter, may be, for example, corrected using the measurement value of the speckle size. This makes it possible to control a cell size or the like with a high degree of accuracy.

As described above, in the observation system 100 according to the present embodiment, an image signal of the observation target site 2 irradiated with the laser light 11 and on which image-capturing has been performed, is acquired. A cell size of a cell 42 is controlled according to an imaging parameter of the observation target site 2, and using this cell 42, a speckle contrast Cs is calculated using an image signal of the observation target site 2. This makes it possible to calculate a speckle contrast Cs depending on an imaging parameter, and to observe the observation target site 2 with a high degree of accuracy by optimally performing calculation processing, even if there is a change in an image-capturing condition of a camera.

A method for generating an observation image using a speckle contrast calculated in a fixed cell size, is conceivable as a method for observing a tissue of a living body using a speckle pattern. In this case, an observation image in which the lightness and darkness, the resolution, or the like of each site of a tissue of a living body is fixed, is generated. In the case of such a method, it is difficult to cope with, for example, a difference in the type of a tissue of a living body and a change in the characteristics of an optical system, and this may result in reducing accuracy in observation.

For example, Patent Literature 1 discloses using, in the "measurement of deep blood flow using a diffuse speckle contrast analysis", a speckle contrast in the spatial domain and a speckle contrast in the time domain in combination, for the purpose of evaluating blood flow in a tissue. Although the speckle contrast in the time domain exhibits lower time resolution than that of the spatial domain, a region to be used may be smaller, and thus Patent Literature 1 proposes using these speckle contrasts differently. However, Patent Literature 1 does not disclose that the contrast value and the spatial resolution are changed according to a calculation-target space range (cell size) when a speckle contrast in the spatial domain is calculated.

In the first place, it is considered that certain levels of a contrast and a spatial resolution are necessary for a treatment to be applied, and there is a possibility that a good quality of an image will not be acquired except under an optimal calculation condition and thus appropriate diagnosis will not be performed. Further, since a relationship between a calculation condition, and a contrast value and a spatial resolution depends on the f-number and the optical magnification of an observation optical system of a light source, there is a possibility that, even if a calculation condition is once optimized, the optimized calculation condition will not be an optimal calculation condition due to a process such as zoom or a change in a stop being performed during observation. Further, since there is a possibility that an optical parameter will be changed when a lens is changed, it is considered that a correction mode for updating information regarding an optimal calculation condition is necessary.

In the present embodiment, a speckle size is calculated by the block control section 35 using an imaging parameter, and a cell size is controlled according to the speckle size. This makes it possible to optimize a cell size according to the size of a speckle observed in the observation target site 2. Thus, for example, it becomes possible to generate an observation image in a proper cell size depending on the characteristics of an optical system of, for example, the camera 20. This results in being able to observe the observation target site 2 with a high degree of accuracy.

Further, in the present embodiment, the selection of an image quality mode related to the image quality of an observation image is received by the UI acquisition section 34. The size of a cell 42 is controlled by the block control section 35 according to the selected image quality mode. For example, an operator can select a desired image quality mode from among a plurality of image quality modes of differently weighted combinations of a resolution and a contrast, according to, for example, the type of a tissue of a living body. This makes it possible to generate an observation image with an image quality desired by an operator, and to observe a site of interest such as the blood vessel 71 and the aneurysm 72 with a high degree of accuracy.

In each image quality mode, the cell size is controlled by the block control section 35 such that a display luminance of each portion of an observation image is substantially constant. This makes it possible to control the cell size by giving feedback one by one such that the cell size has an optimal value even if there is a change in an optical element for determining a speckle diameter during observation (an f-number and a zoom magnification of the lens section 21). Thus, it becomes possible to magnify or demagnify the observation target site 2 during observation without changing, for example, a display luminance of the blood vessel 71 or a site around the blood vessel 71. This results in being able to observe the observation target site 2 in detail, and to sufficiently improve the accuracy in observation.

In the present embodiment, the processing size table 38 of the observation system 100 is corrected using a standard scatterer. This makes it possible to properly correct the processing size table 38 according to an optical system for observation even if, for example, there is a change in the optical system due to a replacement of, for example, the lens section 21. This makes it possible to properly control the cell size, and to provide a precise observation image.

Further, the selection of the automatic recognition mode (refer to FIG. 16) makes it possible to automatically set an optimal cell size according to, for example, the size of the blood vessel 71 of an observation target. This makes it possible to perform observation with an image quality suitable for the characteristics of the observation target site 2 without an operator selecting an image quality by himself/ herself, and to reduce the burden on the operator.

For example, the present technology is applicable to, for example, an endoscope or an optical microscope that is used in the medical and biological fields. In other words, the observation system 100 can also be configured as an endoscope or a microscope.

In this case, examples of the observation target site 2 include tissues of a living body such as a cell, a tissue, and an organ of a living body. The use of the present technology makes it possible to observe a tissue of a living body with a high degree of accuracy. For example, it is possible to observe a tissue of a living body with a high degree of accuracy by performing the processes illustrated in FIG. 16 using imaging parameters such as an f-number and an optical magnification of a lens system used in, for example, an endoscope or an optical microscope.

Other Embodiments

The present technology is not limited to the embodiments described above, and may achieve other various embodiments.

In the description above, a speckle size is calculated using an imaging parameter, and a cell size is controlled according to the speckle size. The present technology is not limited to the case of calculating a speckle size, and a cell size may be directly controlled using an imaging parameter.

It is assumed that, for example, an f-number and an optical magnification are used as imaging parameters. In this case, cell sizes respectively corresponding to a plurality of combinations of an f-number and an optical magnification are recorded in a processing size table for each image quality mode. In other words, the processing size table is created such that, when respective values of an image quality mode, an f-number, and an optical magnification are determined, one corresponding cell size is determined.

As described above, it is possible to control a cell size precisely according to the behavior of a lens section by using a processing size table in which the cell size is set in detail for each imaging parameter. This makes it possible to control, for example, an image quality of an observation image with a high degree of accuracy.

Further, a cell size may be controlled using the contrast map illustrated in FIG. 14, instead of using a processing size table. For example, a contrast map is referred to by a processing size control section. The processing size control section acquires a cell size according to a speckle size from a route corresponding to a target image quality mode in the contrast map. Also in this case, a cell size is controlled properly, and it is possible to generate an observation image with a desired image quality.

Furthermore, The control method and the program according to the present technology may be executed to configure the observation system according to the present technology, by a computer operated by, for example, an operator and another computer capable of performing communication through, for example, a network working in conjunction with each other.

In other words, the control method and the program according to the present technology can also be executed not only in a computer system constituted of a single computer, but also in a computer system in which plural computers operate in conjunction with one another. Note that, in the present disclosure, a system refers to a set of a plurality of elements (such as devices and modules (components)), and whether all of the elements are in a single housing is no object. Thus, a plurality of devices accommodated in separate housings and connected to one another through a network, and a single device in which a plurality of modules is accommodated in a single housing are both systems.

Regarding, for example, a process of acquiring an image signal; a process of controlling the size of a pixel block; and a process of calculating speckle data, the executing, in the computer system, the control method and the program according to the present technology includes causing a single computer to perform the processes and causing different computers to perform the respective processes. Further, performing the respective processes by a specified computer includes causing another computer to perform a portion of or all of the processes and acquiring a result of it.

In other words, the control method and the program according to the present technology are also applicable to a configuration of cloud computing in which a plurality of devices shares tasks of a single function and works collaboratively to perform the single function through a network.

At least two of the features of the present technology described above can also be combined. In other words, various features described in the respective embodiments may be optionally combined regardless of the embodiments. Further, the various effects described above are not limitative but are merely illustrative, and other effects may be provided.

Note that the present technology may also take the following configurations.

(1) A control device including:

an acquisition section that acquires an image signal of a tissue of a living body irradiated with laser light and on which image-capturing has been performed;

a block control section that controls a size of a pixel block according to an image-capturing condition for the image-capturing on the tissue of a living body; and a calculator that calculates speckle data based on the acquired image signal, using the pixel block of which the size is controlled.

(2) The control device according to (1), further including a generator that generates an observation image of the tissue of a living body using the speckle data.

(3) The control device according (2), in which the speckle data includes a speckle contrast, and the generator generates the observation image using the speckle contrast.

(4) The control device according to any one of (1) to (3), in which the image-capturing condition includes at least one of a condition regarding an f-number (an aperture) of an imaging system that performs the image-capturing on the tissue of a living body, or a condition regarding an optical magnification of the imaging system.

(5) The control device according to any one of (1) to (4), in which the block control section calculates a speckle size using the image-capturing condition, and controls the size of the pixel block according to the calculated speckle size.

(6) The control device according to any one of (2) to (5), further including a storage that stores therein a control table in which the image-capturing condition is associated with the size of the pixel block.

(7) The control device according to any one of (2) to (6), in which the block control section controls the size of the pixel block such that a specified display parameter related to a display luminance of the observation image is kept substantially constant.

(8) The control device according to (7), further including a mode reception section that receives a selection of an image quality mode related to an image quality of the observation image, in which the block control section controls the size of the pixel block depending on the selected image quality mode.

(9) The control device according to (8), in which the mode reception section receives an image quality mode related to a display resolution of the observation image.

(10) The control device according to (9), in which the mode reception section receives a plurality of image quality modes different from one another, and the block control section controls the size of the pixel block such that the specified display parameter related to the display luminance of the observation image is kept substantially constant in ranges that are different with respect to respective image quality modes of the plurality of image quality modes.

(11) The control device according to (10), in which the plurality of image quality modes includes a first image quality mode and a second image quality mode, in which, from among the display luminance and the display resolution of the observation image, priority is given to the display luminance in the first image quality mode, and priority is given to the display resolution in the second image quality mode.

(12) The control device according to any one of (6) to (11), in which the storage stores therein the control table in which a correspondence relationship among the image-capturing condition, the size of the pixel block, and the image quality mode related to an image quality of the observation image.

(13) The control device according to any one of (6) to (12), in which the control table is generated using a specified target for correction.

(14) The control device according to any one of (1) to (13), in which the block control section controls the size of the pixel block depending on a size of a blood vessel in an image-capturing range of the tissue of a living body.

(15) The control device according to any one of (1) to (14), in which the control device is configured as an endoscope or a microscope.

(16) A control method performed by a computer system, the control method including:
acquiring an image signal of a tissue of a living body irradiated with laser light and on which image-capturing has been performed;
controlling a size of a pixel block according to an image-capturing condition for the image-capturing on the tissue of a living body; and
calculating speckle data based on the acquired image signal, using the pixel block of which the size is controlled.

(17) A program that causes a computer system to perform a process including:
acquiring an image signal of a tissue of a living body irradiated with laser light and on which image-capturing has been performed;
controlling a size of a pixel block according to an image-capturing condition for the image-capturing on the tissue of a living body; and
calculating speckle data based on the acquired image signal, using the pixel block of which the size is controlled.

REFERENCE SIGNS LIST 2 observation target site
11 laser light
20 camera
21 lens section
30 controller
32 image acquisition section
33 camera control section
34 UI acquisition section
35 block control section
36 speckle calculation section
37 storage
38 processing size table
40 predicted-speckle-size calculator
41 processing-size control section
42, 42a-42e cell
50, 50a-50d speckle image
60, 60a-60h speckle contrast image
62 contrast map
71, 71a-71c blood vessel
72 aneurysm
100 observation system

The invention claimed is:
1. A control device, comprising:
circuitry configured to:
acquire an image signal of a tissue of a living body, wherein
the tissue of the living body is irradiated with laser light, and
an image-capturing process is performed on the tissue of the living body;

receive a selection of an image quality mode from a plurality of image quality modes, wherein
the plurality of image quality modes is related to a display resolution of an observation image, and
each of the plurality of image quality modes is different;
control a size of a pixel block based on the selected image quality mode and an image-capturing condition for the image-capturing process on the tissue of the living body, wherein
a display parameter related to a display luminance of the observation image is constant in a plurality of ranges, and
each range of the plurality of ranges is different with respect to respective image quality mode of the plurality of image quality modes;
calculate speckle data based on the acquired image signal and the controlled size of the pixel block; and
generate the observation image of the tissue of the living body based on the calculated speckle data.

2. The control device according to claim 1, wherein the speckle data includes a speckle contrast, and
the circuitry is further configured to generate the observation image based on using the speckle contrast.

3. The control device according to claim 1, wherein the image-capturing condition includes at least one of a condition related to an f-number or an aperture of an imaging system that performs the image-capturing process on the tissue of the living body, or a condition related to an optical magnification of the imaging system.

4. The control device according to claim 1, wherein the circuitry is further configured to:
calculate a speckle size based on the image-capturing condition; and
control the size of the pixel block based on to the calculated speckle size.

5. The control device according to claim 1, further comprising a storage configured to store a control table, wherein the control table includes the image-capturing condition associated with the size of the pixel block.

6. The control device according to claim 5, wherein the control table includes a correspondence relationship among the image-capturing condition, the size of the pixel block, and the selected image quality mode.

7. The control device according to claim 5, wherein the control table is generated based on a target for correction.

8. The control device according to claim 1, wherein
the plurality of image quality modes includes a first image quality mode and a second image quality mode,
from among the display luminance of the observation image and the display resolution of the observation image, priority is given to the display luminance in the first image quality mode, and priority is given to the display resolution in the second image quality mode.

9. The control device according to claim 1, wherein the circuitry is further configured to control the size of the pixel block based on a size of a blood vessel in an image-capturing range of the tissue of the living body.

10. The control device according to claim 1, wherein the control device is configured as one of an endoscope or a microscope.

11. A control method, comprising:
acquiring an image signal of a tissue of a living body, wherein
the tissue of the living body is irradiated with laser light, and
an image-capturing process is performed on the tissue of the living body;
receiving a selection of an image quality mode from a plurality of image quality modes, wherein
the plurality of image quality modes is related to a display resolution of an observation image, and
each of the plurality of image quality modes is different;
controlling a size of a pixel block based on the selected image quality mode and an image-capturing condition for the image-capturing process on the tissue of the living body, wherein
a display parameter related to a display luminance of the observation image is constant in a plurality of ranges, and
each range of the plurality of ranges is different with respect to respective image quality mode of the plurality of image quality modes;
calculating speckle data based on the acquired image signal and the controlled size of the pixel block; and
generating the observation image of the tissue of the living body based on the calculated speckle data.

12. A non-transitory computer-readable medium having stored thereon, computer-executable instructions which, when executed by a processor, cause the processor to execute operations, the operations comprising:
acquiring an image signal of a tissue of a living body, wherein
the tissue of the living body is irradiated with laser light, and
an image-capturing process is performed on the tissue of the living body;
receiving a selection of an image quality mode from a plurality of image quality modes, wherein
the plurality of image quality modes is related to a display resolution of an observation image, and
each of the plurality of image quality modes is different;
controlling a size of a pixel block based on the selected image quality mode and an image-capturing condition for the image-capturing process on the tissue of the living body, wherein
a display parameter related to a display luminance of the observation image is constant in a plurality of ranges, and
each range of the plurality of ranges is different with respect to respective image quality mode of the plurality of image quality modes;
calculating speckle data based on the acquired image signal and the controlled size of the pixel block; and
generating the observation image of the tissue of the living body based on the calculated speckle data.

* * * * *